(12) United States Patent
Jain et al.

(10) Patent No.: US 11,718,621 B2
(45) Date of Patent: Aug. 8, 2023

(54) TEBIPENEM PIVOXIL CRYSTALLINE FORMS, COMPOSITIONS INCLUDING THE SAME, METHODS OF MANUFACTURE, AND METHODS OF USE

(71) Applicant: SPERO THERAPEUTICS, INC., Cambridge, MA (US)

(72) Inventors: Akash Jain, Cambridge, MA (US); Evan Hecker, Cambridge, MA (US); Richard Edwards, Cambridge (GB); Thierry Bonnaud, Cambridge (GB)

(73) Assignee: SPERO THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 17/136,759

(22) Filed: Dec. 29, 2020

(65) Prior Publication Data

US 2021/0122753 A1    Apr. 29, 2021

Related U.S. Application Data

(63) Continuation of application No. 16/483,989, filed as application No. PCT/US2018/017067 on Feb. 6, 2018, now Pat. No. 10,889,587.

(60) Provisional application No. 62/455,109, filed on Feb. 6, 2017.

(51) Int. Cl.
*C07D 477/20* (2006.01)
*A61K 45/06* (2006.01)
*A61P 31/04* (2006.01)

(52) U.S. Cl.
CPC ............ *C07D 477/20* (2013.01); *A61K 45/06* (2013.01); *C07B 2200/13* (2013.01)

(58) Field of Classification Search
CPC .. C07D 477/20; A61K 45/06; C07B 2200/13; A61P 31/04; A61P 31/431
See application file for complete search history.

(56) References Cited

U.S. PATENT DOCUMENTS 5,886,172 A    3/1999    Abe et al.

FOREIGN PATENT DOCUMENTS

| AU | 2018215687 | | 12/2020 |
|---|---|---|---|
| CN | 102558181 | * | 12/2010 |
| CN | 102558181 A | | 7/2012 |
| CN | 102952125 A | | 3/2013 |
| JP | 0853453 A | | 2/1996 |
| JP | H10195076 | * | 7/1998 |
| JP | 2011504495 A | | 2/2011 |
| KR | 100930586 B1 | | 12/2009 |
| WO | 2018112372 A1 | | 6/2018 |

OTHER PUBLICATIONS

CN 102558181 machine translation, 2022, machine translation of CN 102558181.*
Aitipamula, et al., "Polymorphism: Fundamentals and Applications," Supramolecular Chemistry: From Molecules to Nanomaterials; (2012), 1-18.
Balbach et al., "Pharmaceutical Evaluation of Early Development Candidates, The 100 mg approach," International Journal of Pharmaceutics, (2004), vol. 275, 1-12.
Berge et al., "Pharmaceutical Salts," Journal of Pharmaceutical Sciences, (1977), vol. 66, (No. 1), 1-19.
Toyokura et al., "The Science of Polymorphism and Crystallization of Pharmaceuticals, Trends in Development, Production and Regulation," Maruzen Planet Co., Ltd. (2002), 305-317.
Rohani, "Applications of the Crystallization Process in the Pharmaceutical Industry," Frontiers of Chemical Engineering in China, (2010), vol. 4, (No. 1:2-9), Abstract Only, 2 pages.
Serajuddin, "Bioavailability Enhancement of Poorly Water-Soluble Drugs by Solid Dispersion in Surface Active and Self-Emulsifying Vehicles," Pharmaceutics R & D Dept., Bristol-Myers Squibb Pharmaceutical Research Institute, (1997), (No. 90), 43-50.
Serajuddin, "Salt Formation to Improve Drug Solubility," Science Direct, Advanced Science Direct Reviews, (2007), vol. 59, 603-616.
Serajuddin, "Solid Dispersion of Poorly Water-Soluble Drugs: Early Promises, Subsequent Problems, and Recent Breakthroughs," Journal of Pharmaceutical Sciences, (1999), vol. 88, (No. 10), 1058-1066.

\* cited by examiner

*Primary Examiner* — Sun Jae Yoo
(74) *Attorney, Agent, or Firm* — Cantor Colburn LLP

(57) ABSTRACT

The disclosure is directed to new crystalline tebipenem pivoxil salt forms, including a crystalline tebipenem pivoxil ethane sulfonate salt form (Form A), a crystalline tebipenem pivoxil ketoglutarate salt form (Form A), tebipenem pivoxil maleate salt forms (Form A and Form B), a tebipenem pivoxil malate salt form (Form A), a tebipenem pivoxil methane sulfonate salt form (Form B), a tebipenem pivoxil hydrobromide salt form (Form B), and a tebipenem pivoxil edisylate salt form (Form A). The disclosure also includes a composition, comprising a crystalline tebipenem pivoxil salt and a pharmaceutically acceptable carrier and further includes a method for treating an antibiotic resistant bacterial infection, comprising administering to a patient in need of such treatment a therapeutically effective amount of a crystalline tebipenem pivoxil salt.

16 Claims, 28 Drawing Sheets

TEBIPENEM PIVOXIL CRYSTALLINE FORMS, COMPOSITIONS INCLUDING THE SAME, METHODS OF MANUFACTURE, AND METHODS OF USE

CROSS REFERENCE TO RELATED APPLICATIONS

This application is a continuation of U.S. application Ser. No. 16/483,989, filed Aug. 6, 2019, which is a National Stage application of PCT/US2018/017067, filed Feb. 6, 2018, which claims priority to U.S. Provisional Application No. 62/455,109, filed Feb. 6, 2017, and all the benefits accruing therefrom under 35 U.S.C. § 119, the contents of each of which are incorporated by reference in their entirety.

FIELD OF THE DISCLOSURE

Disclosed are solid tebipenem pivoxil salt forms, including crystalline forms, pharmaceutical compositions and preparations containing the solid tebipenem pivoxil salt forms, methods for using the crystalline forms to treat bacterial infections, and methods of manufacture of the crystalline forms.

BACKGROUND

The molecules in a crystalline solid are arranged in a crystal lattice, a three dimensional structure in which structural units (unit cells) are repeated in a regular manner Different crystal forms of the same substance (polymorphs) have distinct crystal lattices, which can result in important differences in their properties, utilities, and commercial values. For example, graphite and diamond are polymorphs of crystalline carbon. Polymorphs of pharmaceutical compounds can also be distinctly, if not as dramatically, different in their properties, including properties relevant to the development of formulations of such pharmaceutical compounds and to the development of solid dosage forms, such as tablets and capsules, comprising such formulations. The crystal form of a drug may also be relevant to compliance with regulatory requirements concerning its manufacture.

Tebipenem pivoxil is a carbapenem antibiotic useful for treating antibiotic resistant bacterial infections. To improve therapeutic use of tebipenem pivoxil, new solid forms, such as crystalline salt forms, are desirable.

SUMMARY

Disclosed herein are crystalline tebipenem pivoxil salt forms. These crystalline forms include a crystalline tebipenem pivoxil ethane sulfonate salt form (Form A), a crystalline tebipenem pivoxil ketoglutarate salt form (Form A), tebipenem pivoxil maleate salt forms (Form A and Form B), a tebipenem pivoxil malate salt form (Form A), a tebipenem pivoxil methane sulfonate salt form (Form B), a tebipenem pivoxil hydrobromide salt form (Form B), and a tebipenem pivoxil edisylate salt form (Form A).

Also disclosed herein is a composition, comprising a crystalline tebipenem pivoxil salt and a pharmaceutically acceptable carrier.

Also disclosed herein is a method for treating an antibiotic resistant bacterial infection, comprising administering to a patient in need of such treatment a therapeutically effective amount of a crystalline tebipenem pivoxil salt.

Methods of manufacturing crystalline tebipenem pivoxil salt forms are also included.

BRIEF DESCRIPTION OF THE DRAWINGS

The above and other aspects, advantages and features of this disclosure will become more apparent by describing in further detail exemplary embodiments thereof with reference to the accompanying drawings.

DETAILED DESCRIPTION

Figure 1:
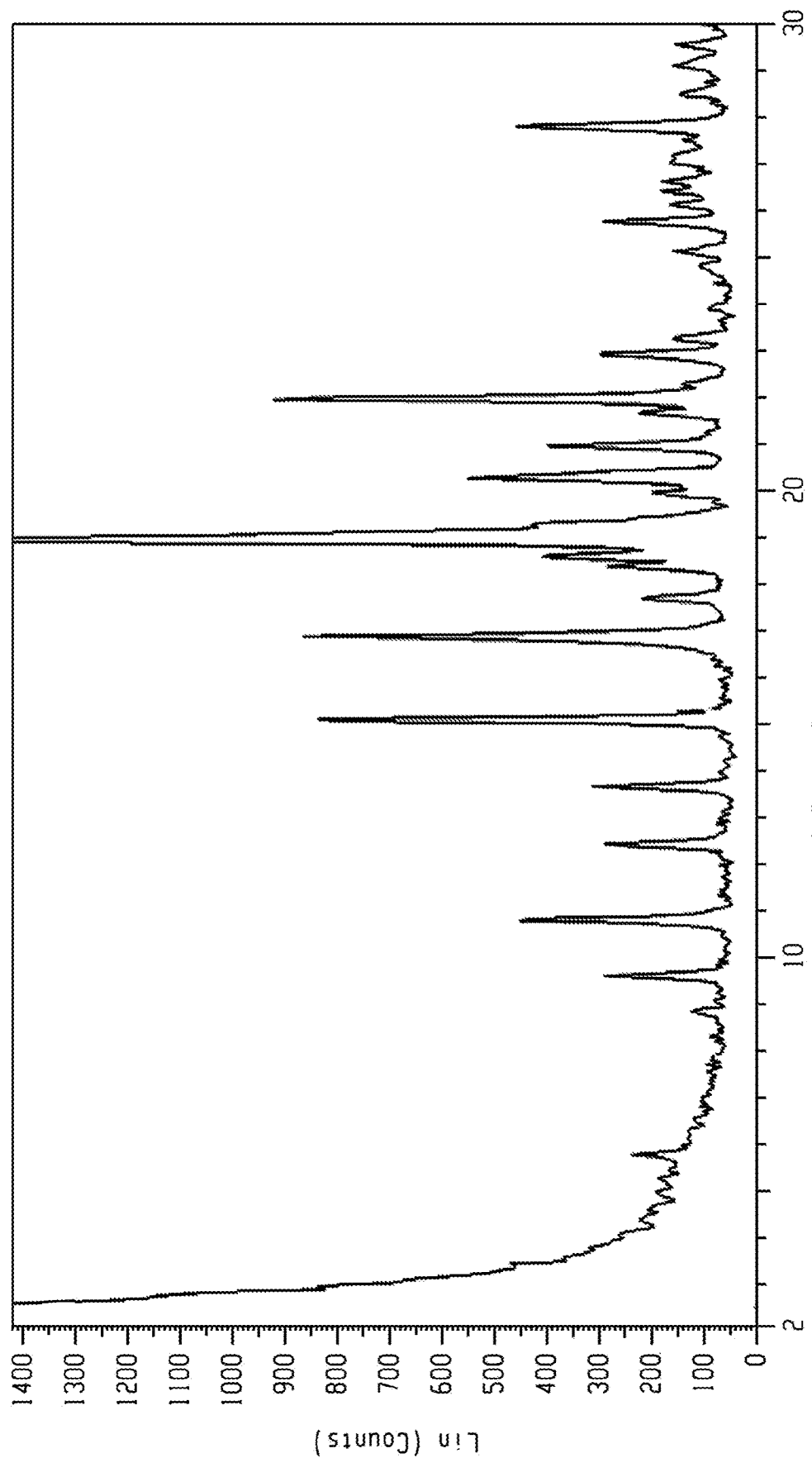
FIG. 1. XRPD diffractogram of crystalline tebipenem pivoxil ethane sulfonate Form A.

The disclosure now will be described in more detail, with reference to the accompanying figures. This disclosure may, however, be embodied in many different forms, and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

Terminology

A "dosage form" means a unit of administration of an active agent. Examples of dosage forms include tablets, capsules, injections, suspensions, liquids, emulsions, creams, ointments, suppositories, inhalable forms, transdermal forms, and the like.

"Pharmaceutical compositions" are compositions comprising at least one active agent, e.g., a crystalline tebipenem pivoxil salt, and at least one other substance, such as a carrier, excipient, or diluent. Pharmaceutical compositions meet the U.S. FDA's GMP (good manufacturing practice) standards for human or non-human drugs.

The term "carrier" applied to pharmaceutical compositions described herein refers to a diluent, excipient, or vehicle with which an active compound is provided.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

A "patient" is a human or non-human animal in need of medical treatment. Medical treatment can include treatment of an existing condition, such as a disease or disorder, prophylactic or preventative treatment, or diagnostic treatment. In some embodiments the patient is a human patient.

"Providing" means giving, administering, selling, distributing, transferring (for profit or not), manufacturing, compounding, or dispensing.

"Providing a crystalline tebipenem pivoxil salt form" with at least one additional active agent" means a crystalline tebipenem pivoxil salt form and the additional active agent(s) are provided simultaneously in a single dosage form, provided concomitantly in separate dosage forms, or provided in separate dosage forms for administration separated by some amount of time that is within the time in which both the tebipenem pivoxil and the at least one additional active agent are within the blood stream of a patient. The crystalline tebipenem pivoxil salt form and the additional active agent need not be prescribed for a patient by the same medical care worker. The additional active agent or agents need not require a prescription. Administration of crystalline tebipenem pivoxil salt form or the at least one additional active agent can occur via any appropriate route, for example, oral tablets, oral capsules, oral liquids, inhalation, injection, suppositories or topical contact.

"Treatment," as used herein includes providing the crystalline tebipenem pivoxil salt form and at least one additional active agent sufficient to: (a) reduce probability a disease or a symptom of a disease from occurring in a patient who is be predisposed to the disease but has not yet been diagnosed as having it (e.g. prevent bacterial infection in a patient traveling to an area where risk of exposure to bacterial infection is high); (b) inhibiting the disease, i.e. arresting its development; and (c) relieving the disease, i.e., causing regression of the disease. "Treating" and "treatment" also means providing a therapeutically effective amount of the crystalline tebipenem pivoxil salt form and at least one additional active agent to a patient having or susceptible to microbial infection, such as an antibiotic resistant bacterial infection or a Gram negative bacterial infection.

A "therapeutically effective amount" of a pharmaceutical combination of this disclosure means an amount effective, when administered to a patient, to provide a therapeutic benefit such as an amelioration of symptoms, e.g., an amount effective to decrease the symptoms of a bacterial infection. For example a patient infected with a bacterial infection may present abnormal levels of certain blood cells, especially leukocytes (white blood cells) for example, an increase in neutrophils and a decrease in lymphocytes. A therapeutically effect amount is thus an amount sufficient to provide a return of leukocyte levels to the normal range. A therapeutically effective amount is also an amount sufficient to prevent a significant increase or significantly reduce the detectable level of bacteria or bacterial antibodies in the patient's blood, serum, or tissues.

The present disclosure is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

It will be understood that when an element is referred to as being "on" another element, it can be directly on the other element or intervening elements may be present there between. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The tebipenem pivoxil (CAS Reg. No. 161715-24-8) has the following structure (1):

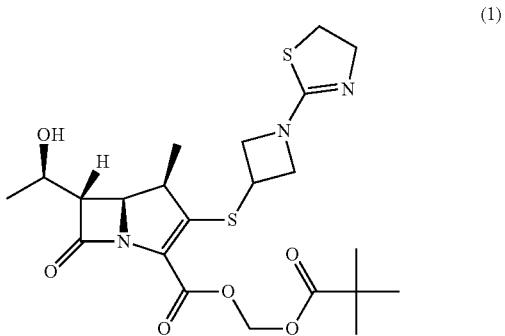 [SMILES: C[C@@H](O)[C@H]1C(=O)N2C(C(=O)OCOC(=O)C(C)(C)C)=C(SC3CN(C4=NCCS4)C3)[C@H](C)[C@H]12]

(1)

Disclosed herein are crystalline forms of a crystalline tebipenem pivoxil ethane sulfonate salt form (Form A), a crystalline tebipenem pivoxil ketoglutarate salt form (Form A), tebipenem pivoxil maleate salt forms (Form A and Form B), a tebipenem pivoxil malate salt form (Form A), a tebipenem pivoxil methane sulfonate salt form (Form B), and a tebipenem pivoxil hydrobromide salt form (Form B).

Crystalline forms of a tebipenem pivoxil salt include single-component and multiple-component crystalline forms, including, but not limited to, polymorphs, solvates, hydrates, co-crystals and clathrates. Some embodiments herein provide single-component crystalline forms of a tebipenem pivoxil salt. Other embodiments herein provide multiple-component crystalline forms comprising a tebipenem pivoxil salt. Multiple-component crystalline forms provided herein include crystalline forms which may be described by the terms salt, co-crystal, hydrate, solvate, clathrate and/or polymorph, and include crystalline forms which may be described by one or more of these terms.

Crystalline forms comprising a tebipenem pivoxil salt can be prepared by the methods described herein, including the methods described in the Examples below, or by techniques known in the art, including heating, cooling, freeze drying, lyophilization, quench cooling the melt, rapid solvent evaporation, slow solvent evaporation, solvent recrystallization, antisolvent addition, slurry recrystallization, crystallization from the melt, desolvation, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid cooling, slow cooling, exposure to solvent and/or water, drying, including, e.g., vacuum drying, vapor diffusion, sublimation, grinding (including, e.g., cryo-grinding, solvent-drop grinding or liquid assisted grinding), microwave-induced precipitation, sonication-induced precipitation, laser-induced precipitation and precipitation from a supercritical fluid. The particle size of the resulting crystalline forms, which can vary, (e.g., from nanometer dimensions to millimeter dimensions), can be controlled, e.g., by varying crystallization conditions, such as, e.g., the rate of crystallization and/or the crystallization solvent system, or by particle-size reduction techniques, e.g., grinding, milling, micronizing or sonication.

While not wishing to be bound by any particular theory, certain crystalline forms are characterized by physical properties, e.g., stability, solubility and dissolution rate, appropriate for pharmaceutical and therapeutic dosage forms. Moreover, while not wishing to be bound by any particular theory, certain crystalline forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain crystalline forms suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

Some embodiments herein provide compositions comprising one or more of the crystalline forms. Other embodiments provide compositions of one or more crystalline forms in combination with other active ingredients. Certain embodiments provide methods of using these compositions in the treatment, prevention or management of diseases and disorders including, but not limited to, the diseases and disorders provided herein.

Crystalline forms provided herein may also include unnatural proportions of atomic isotopes at one or more of the atoms in a tebipenem pivoxil salt. For example, the compound may be radiolabeled with radioactive isotopes, such as for example tritium ($^3$H), iodine-125 ($^{125}$I) sulfur-35 ($^{35}$S), or carbon-14 ($^{14}$C). Radiolabeled compounds are useful as therapeutic agents, e.g., anti-bacterial therapeutic agents, research reagents, e.g., binding assay reagents, and diagnostic agents, e.g., in vivo imaging agents. All isotopic variations of a tebipenem pivoxil salt, whether radioactive or not, are intended to be encompassed within the scope of the embodiments provided herein.

The disclosure includes a crystalline tebipenem pivoxil ethane sulfonate salt form, wherein the XRPD of the form, obtained from a Cu Kα source, has the characteristic 2θ values of FIG. 1 (Form A).

The disclosure includes a crystalline tebipenem pivoxil ethane sulfonate salt form (Form A), wherein the XRPD of the form, obtained from a Cu Kα source, has any 5, 6, 7, 8, 9, 10, 11, 12, or more of the characteristic 2θ values: 5.7, 8.8, 9.6, 10.8, 12.4, 13.7, 15.1, 16.9, 17.8, 18.4, 18.7, 19.0, 19.3, 20.0, 20.3, 21.0, 21.8, 22.1, 22.4, 23.0, 23.4, 24.9, 25.2, 25.9, 26.2, 26.5, 26.8, 27.2, 27.9, 28.6, 29.2, and 29.7+/−0.2 degrees 2θ.

The disclosure includes a crystalline tebipenem pivoxil ethane sulfonate salt form characterized by an XRPD diffractogram obtained from a Cu Kα source which comprises peaks at 2θ values of 9.6, 12.4, 15.1, 19.0, and 20.3+/−0.2 degrees 2θ; or 10.8, 13.7, 16.9, 22.1, and 27.9+/−0.2 degrees 2θ.

Figure 2:
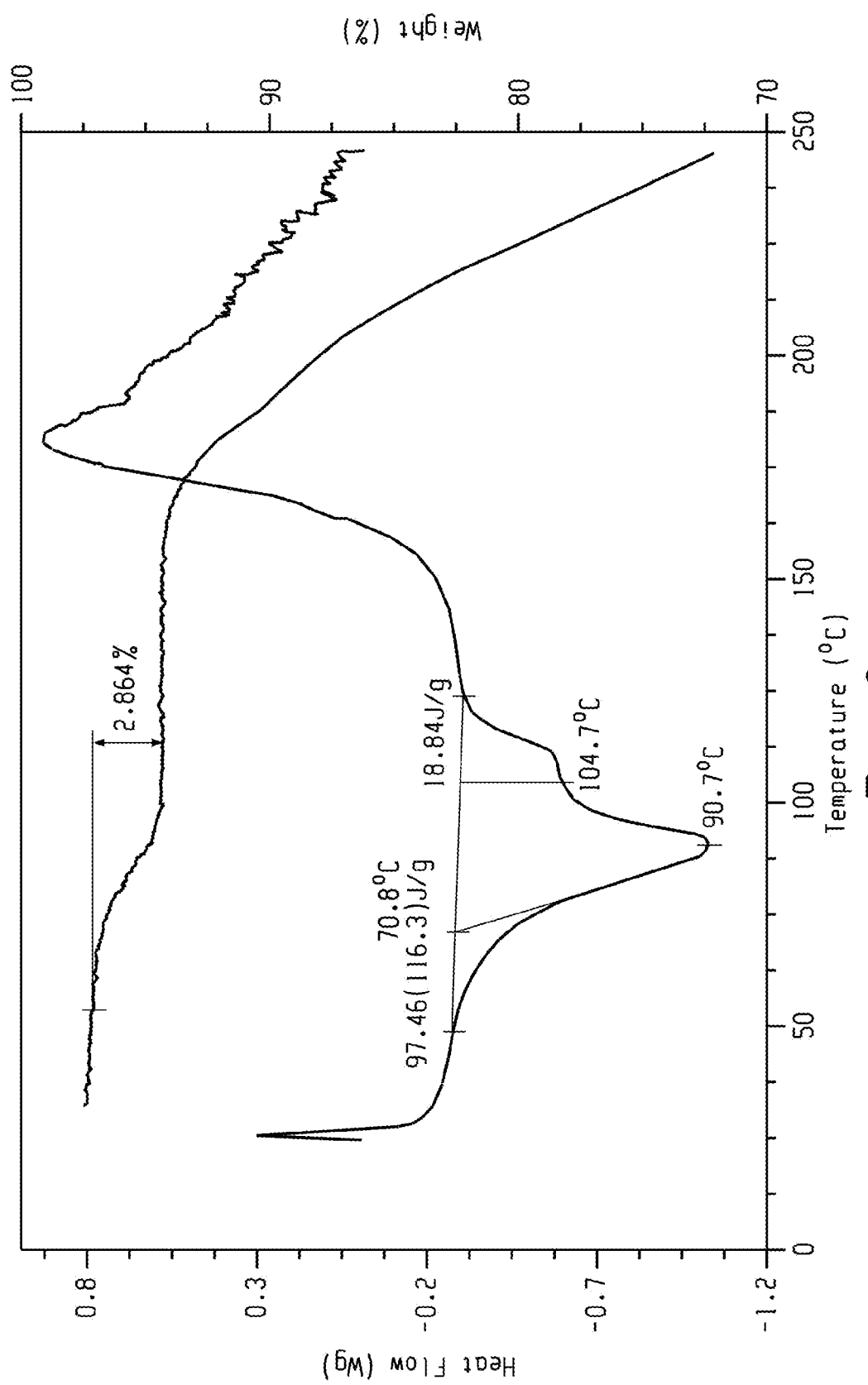
FIG. 2. DSC and TGA profiles of crystalline tebipenem pivoxil ethane sulfonate Form A.

The disclosure includes the crystalline tebipenem pivoxil ethane sulfonate salt form of Form A, additionally characterized by a DSC profile substantially as shown in FIG. 2.

The crystalline tebipenem pivoxil ethane sulfonate salt form of Form A additionally characterized by a DSC profile having an endotherm with an onset of 70.8° C. and a minima of 90.7° C.

Figure 3:
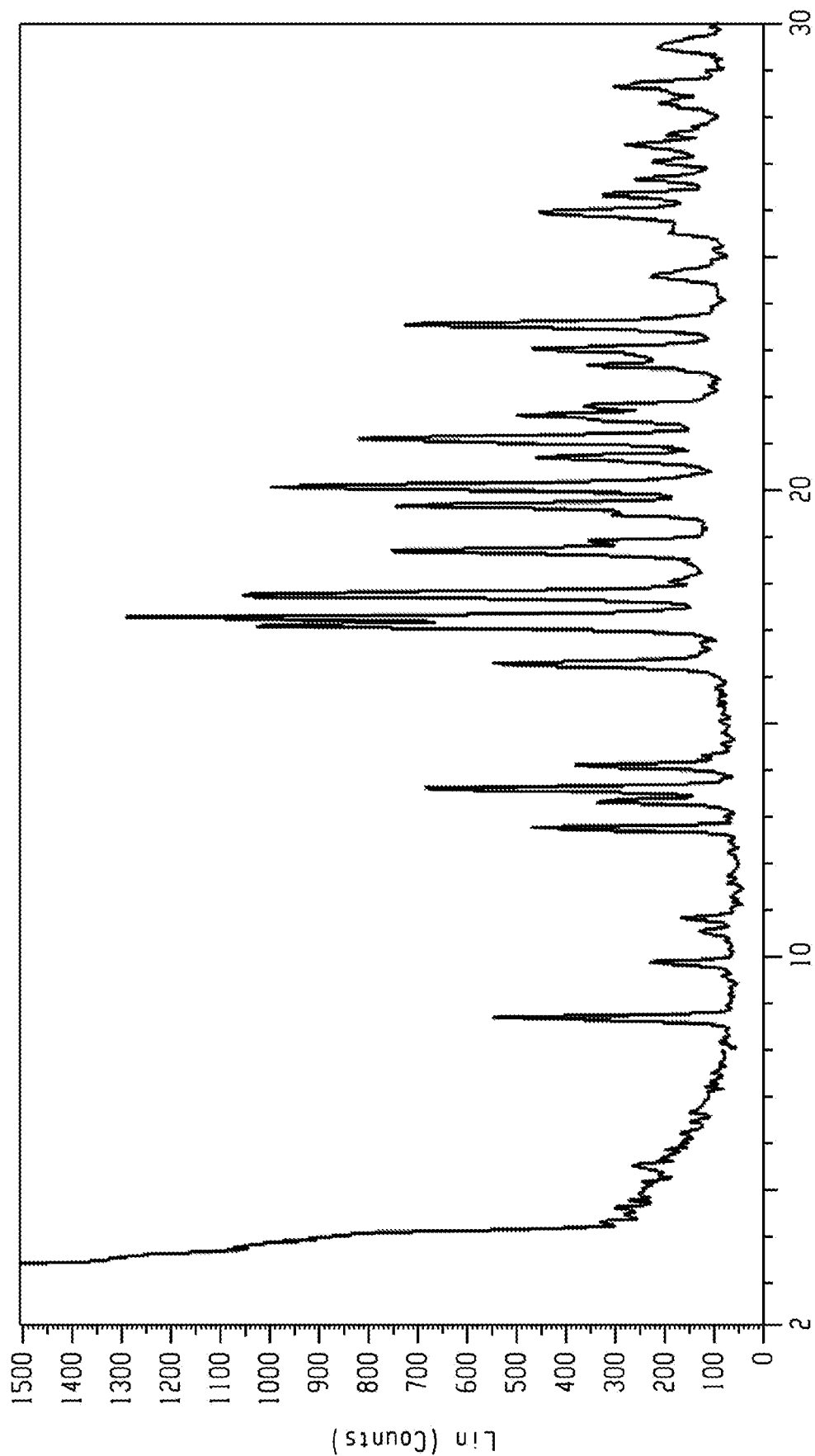
FIG. 3. XRPD diffractogram of crystalline tebipenem pivoxil ketoglutarate salt form A.

The disclosure includes a crystalline tebipenem pivoxil ketoglutarate salt form (Form A), wherein the XRPD of the form, obtained from a Cu Kα source, has the characteristic 2θ values of FIG. 3.

The disclosure includes a crystalline tebipenem pivoxil ketoglutarate salt form (Form A), wherein the XRPD of the form, obtained from a Cu Kα source, has any 5, 6, 7, 8, 9, 10, 11, 12 or more of the following values: 5.4, 8.6, 9.8, 10.4, 10.7, 12.7, 13.2, 13.5, 14.0, 16.2, 17.0, 17.2, 17.7, 18.0, 18.7, 18.9, 19.4, 19.6, 20.0, 20.7, 21.1, 21.6, 21.8, 22.7, 23.0, 23.6, 24.6, 26.7, 27.1, 27.4, 28.3, or 28.7, or 29.6. 29.6

The disclosure includes crystalline tebipenem pivoxil ketoglutarate salt form (Form A), characterized by an XRPD diffractogram obtained from a Cu Kα source which comprises peaks at 2θ values of 8.6, 10.7, 13.2, 16.2, and 17.2+/−0.2 degrees 2θ; or 9.8, 12.7, 13.5, 17.0, and 17.7+/−0.2 degrees 2θ.

Figure 4:
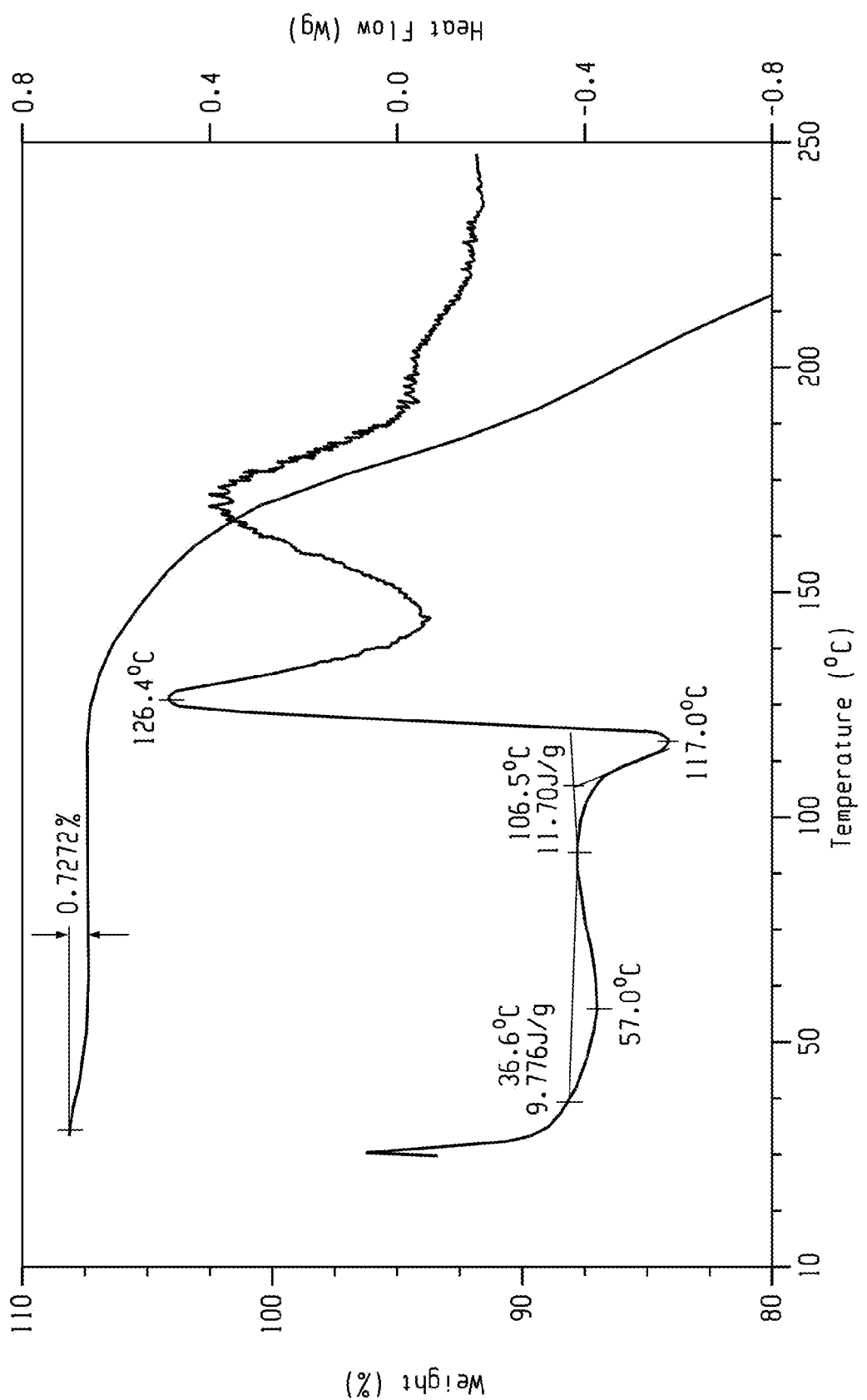
FIG. 4. DSC and TGA profiles of crystalline tebipenem pivoxil ketoglutarate salt Form A.

The crystalline tebipenem pivoxil ketoglutarate salt form of Form A, additionally characterized by a DSC profile having a DSC profile substantially as shown in FIG. 4.

The crystalline tebipenem pivoxil ketoglutarate salt form of Form A, additionally characterized by a DSC profile having an endotherm with an onset of 36.6° C. and a minima of 57.0° C. and a second endotherm with an onset of 106.5° C. and a minima of 117° C.

Figure 5:
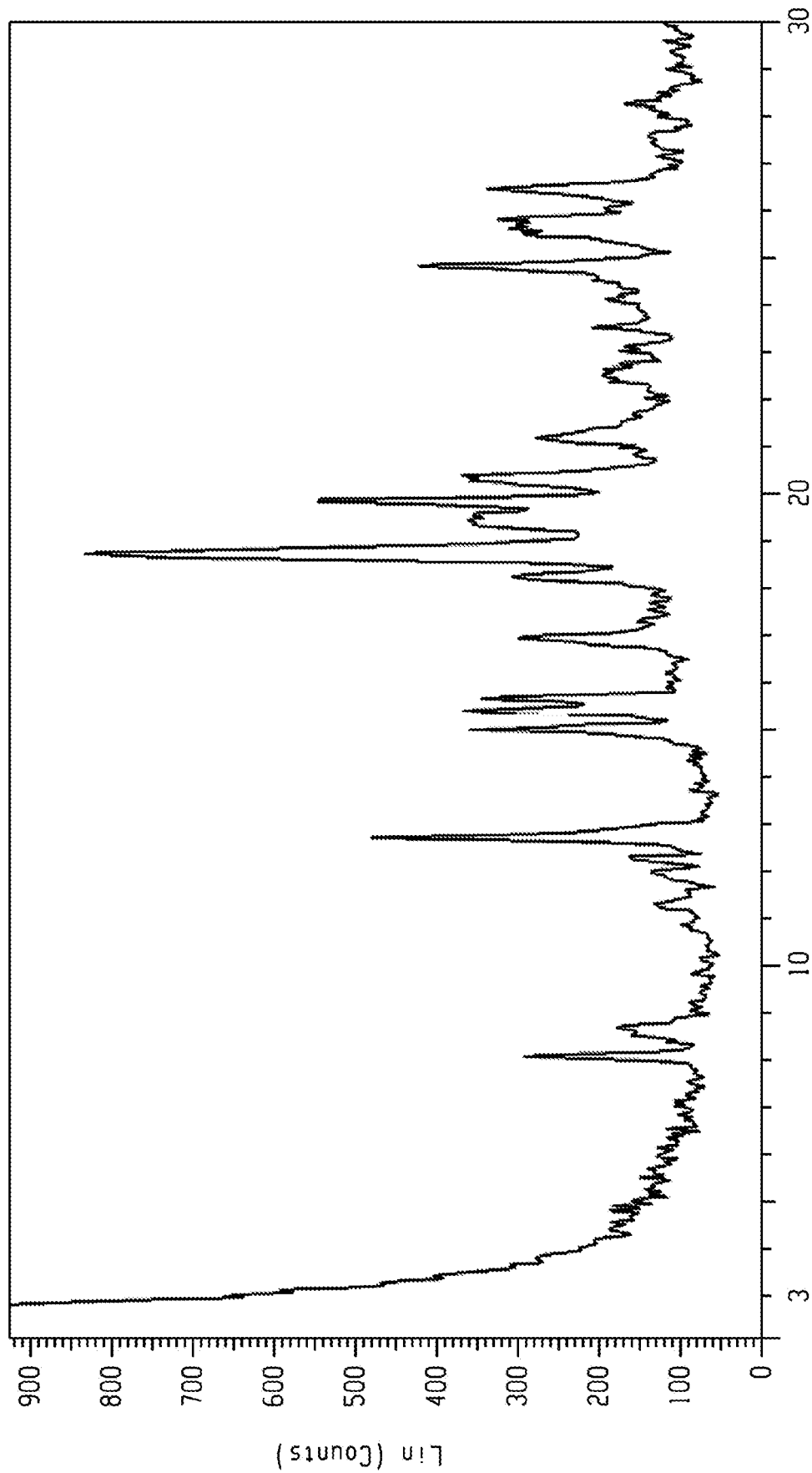
FIG. 5. XRPD diffractogram of crystalline tebipenem pivoxil maleate salt form A.

The disclosure includes a crystalline tebipenem pivoxil maleate salt form, wherein the XRPD of the form, obtained from a Cu Kα source, has the characteristic 2θ values of FIG. 5 (Form A).

The disclosure includes a crystalline tebipenem pivoxil maleate salt form (Form A), wherein the XRPD of the form, obtained from a Cu Kα source, has any 5, 6, 7, 8, 9, 10, 11, 12 or more of the following values: 8.0, 8.6, 10.8, 11.2, 11.9, 12.2, 12.6, 15.0, 15.4, 15.7, 16.9, 18.2, 18.7, 19.4, 19.9, 20.4, 21.2, 22.5, 23.1, 24.2, 24.8, 25.7, 26.5, 27.5, or 28.3.

The disclosure includes a crystalline tebipenem pivoxil maleate salt form (Form AO characterized by an XRPD diffractogram obtained from a Cu Kα source which comprises peaks at 2θ values of 8, 12.6, 15.4, 16.0, and 18.7+/−0.2 degrees 2θ; or 8.6, 15.0, 15.7, 19.4, and 19.9+/−0.2 degrees 2θ.

Figure 6:
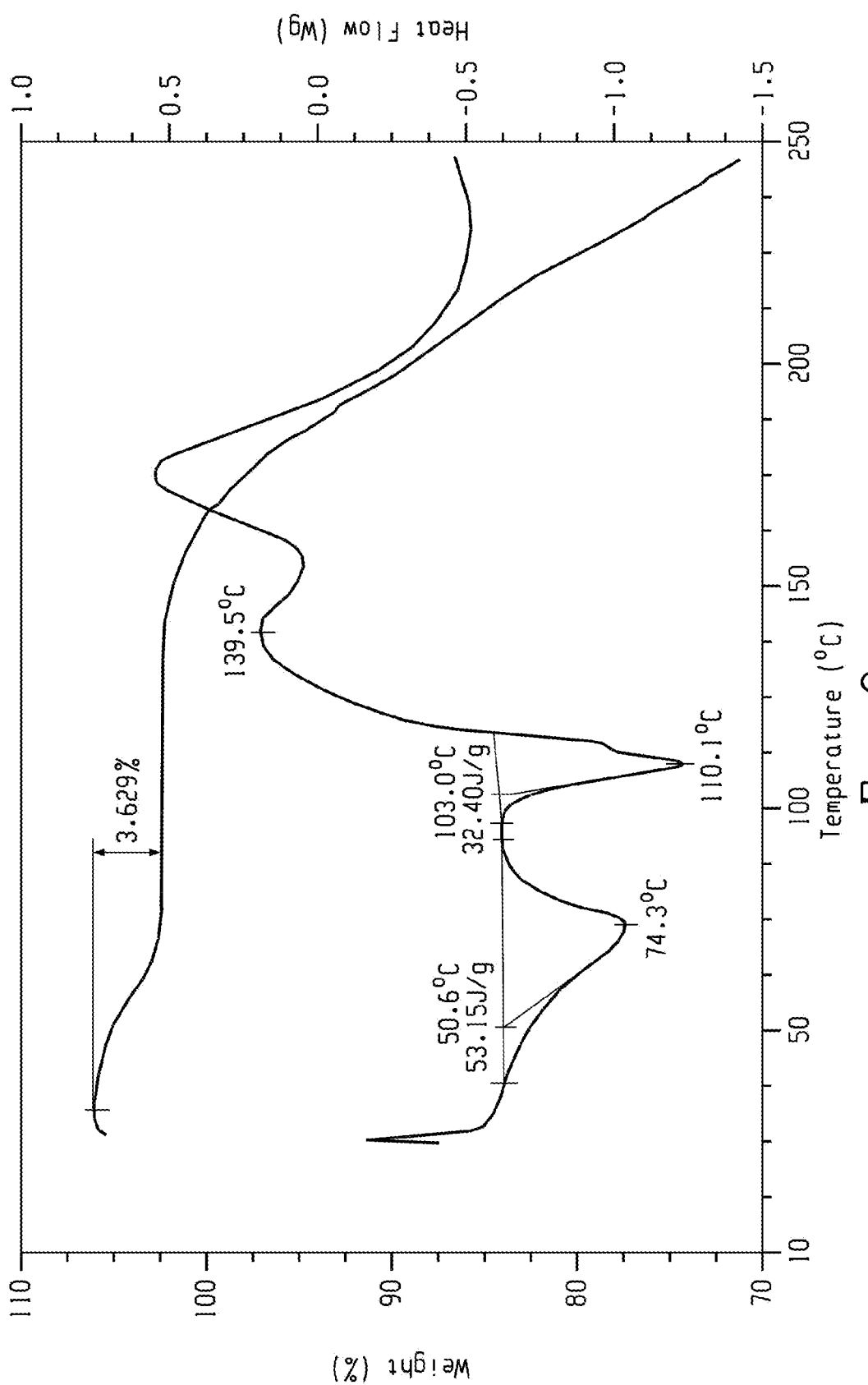
FIG. 6. DSC and TGA profiles of crystalline tebipenem pivoxil maleate salt Form A.

The disclosure includes crystalline tebipenem pivoxil maleate salt Form A, additionally characterized by a DSC profile substantially as shown in FIG. 6.

The disclosure includes crystalline tebipenem pivoxil maleate salt Form A additionally characterized by a DSC profile having an endotherm with an onset of 50.6° C. and a minima of 74.3° C. and a second endotherm with an onset of 103.0° C. and a minima of 110.1° C.

Figure 7:
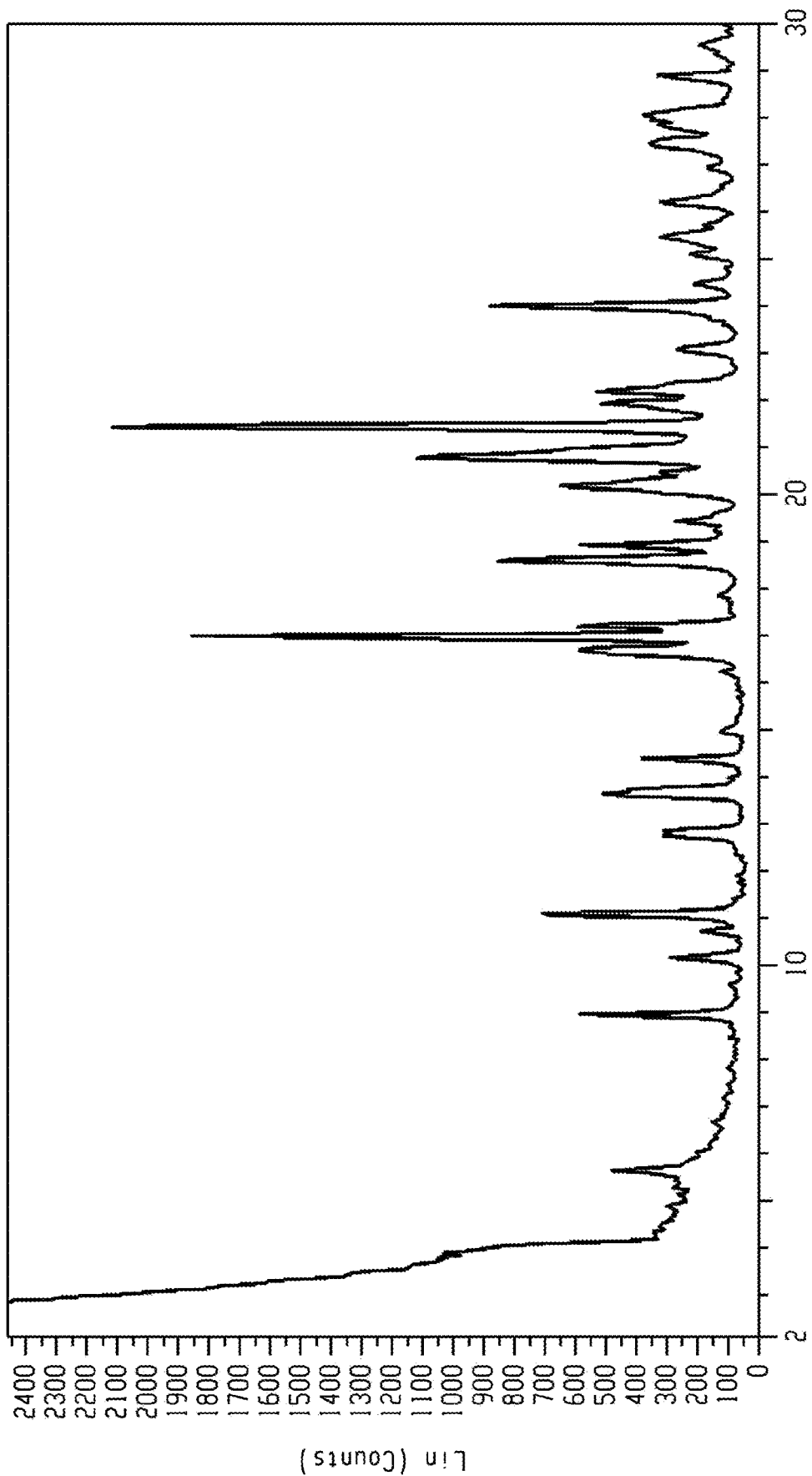
FIG. 7. XRPD diffractogram of crystalline tebipenem pivoxil maleate salt form B.

The disclosure includes a crystalline tebipenem pivoxil maleate salt form, wherein the XRPD of the form, obtained from a Cu Kα source, has the characteristic 2θ values of FIG. 7 (Form B).

The disclosure includes a crystalline tebipenem pivoxil maleate salt form (Form B), wherein the XRPD of the form, obtained from a Cu Kα source, has any 5, 6, 7, 8, 9, 10, 11, 12 or more of the following values: 5.5, 8.9, 10.1, 10.6, 11.0, 12.8, 13.6, 14.3, 14.9, 16.7, 17.0, 17.2, 17.9, 18.6, 19.0, 19.4, 20.2, 20.5, 20.8, 21.4, 21.9, 22.2, 23.1, 24.0, 24.5, 25.1, 25.5, 26.2, 27.5, 28.1, 28.9, or 29.6.

The disclosure includes a crystalline tebipenem pivoxil maleate salt form (Form B) characterized by an XRPD diffractogram obtained from a Cu Kα source which comprises peaks at 2θ values of 8.9, 13.6, 17.0, 18.6, and 20.8+/−0.2 degrees 2θ; or 11.0, 14.3, 19.0, 20.2, and 21.4+/−0.2 degrees 2θ.

Figure 8:
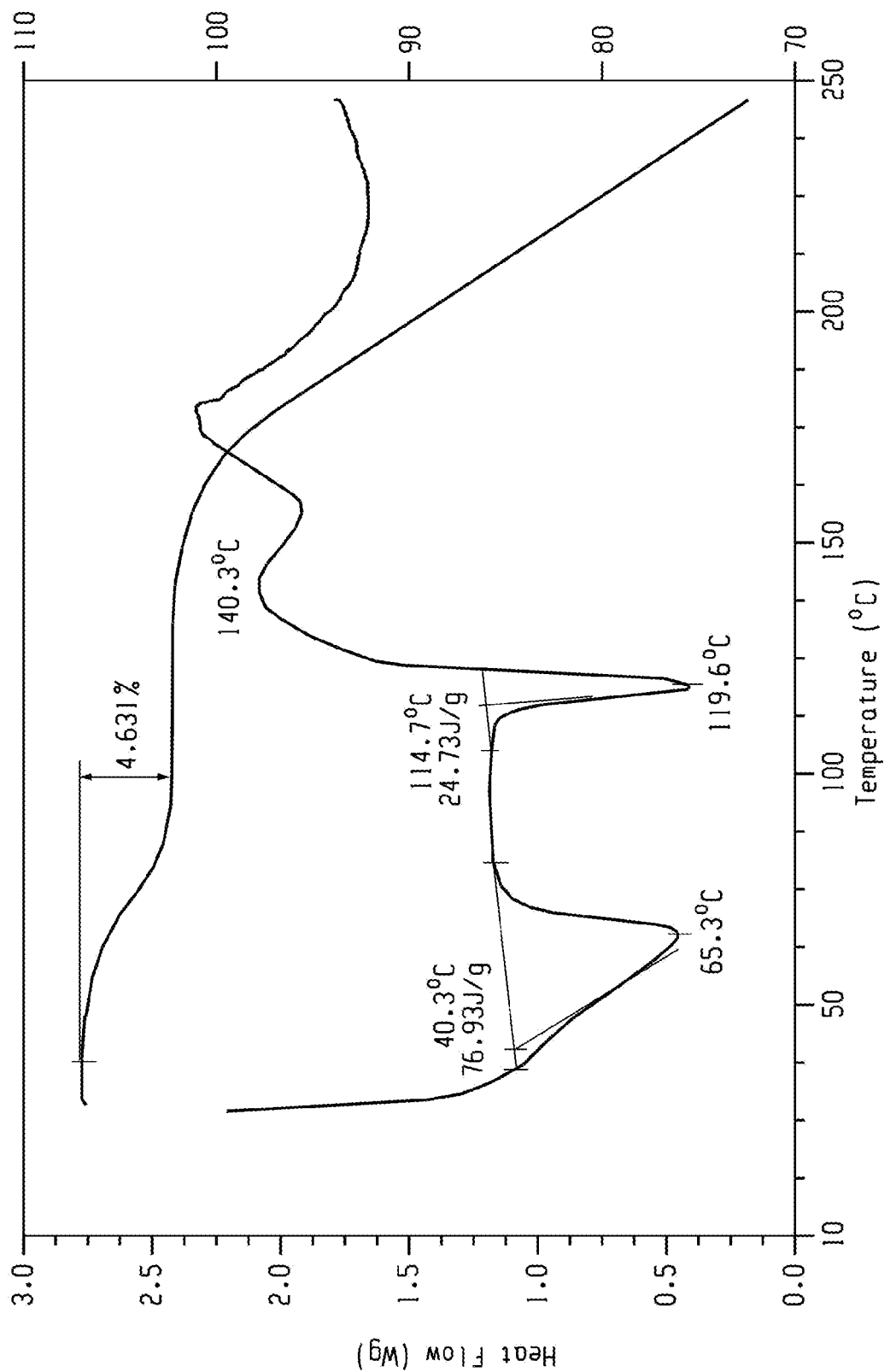
FIG. 8. DSC and TGA profiles of crystalline tebipenem pivoxil maleate salt Form B.

The disclosure includes crystalline tebipenem pivoxil maleate salt form (Form B), additionally characterized by a DSC profile substantially as shown in FIG. 8.

The disclosure includes crystalline tebipenem pivoxil maleate salt Form B additionally characterized by a DSC profile having an endotherm with an onset of 40.3° C. and a minima of 65.3° C. and a second endotherm with an onset of 114.7° C. and a minima of 119.6° C.

Figure 9:
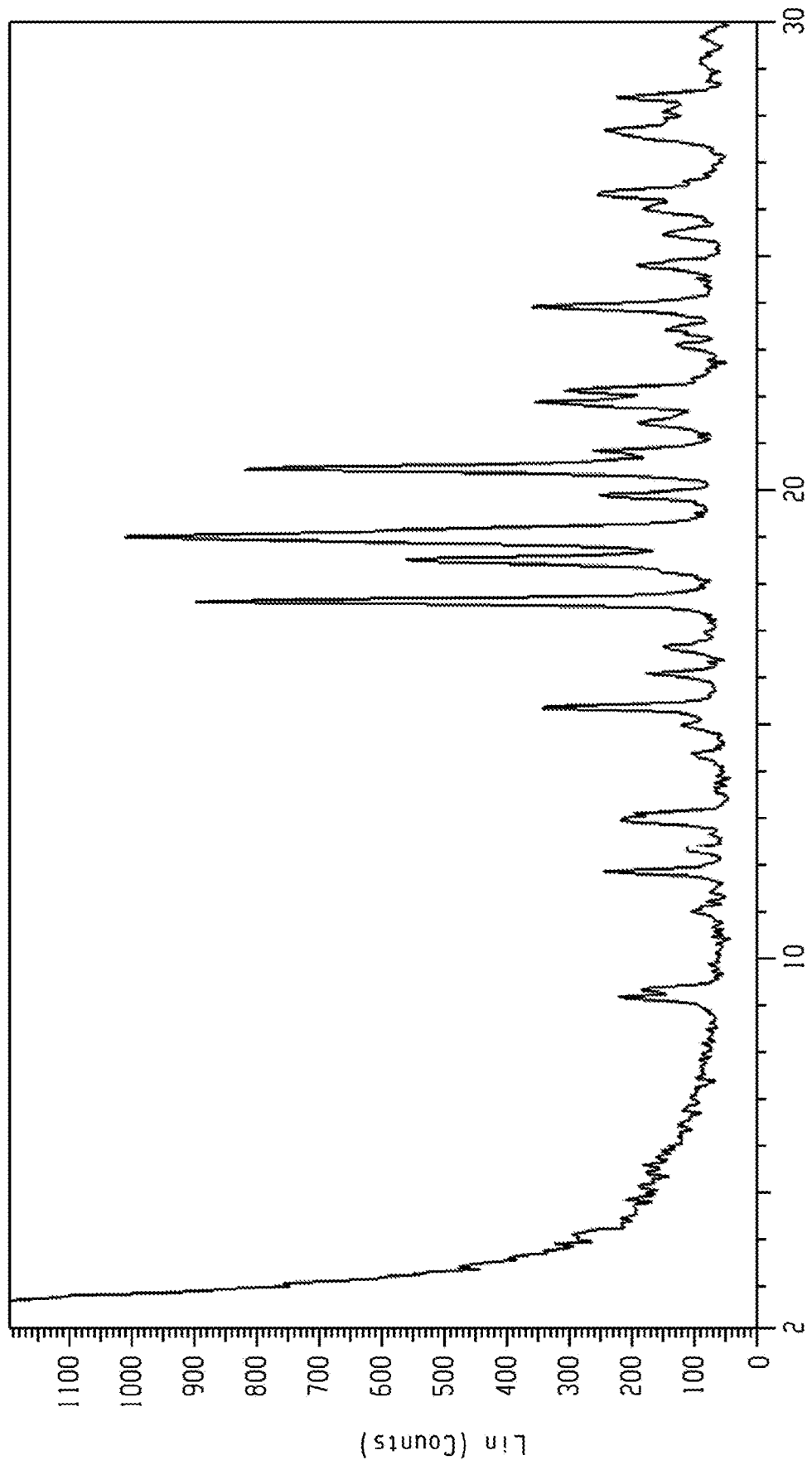
FIG. 9. XRPD diffractogram of crystalline tebipenem pivoxil malate salt Form A prepared by method 1 in which tebipenem pivoxil is dissolved in MeCN.

The disclosure includes crystalline tebipenem pivoxil malate salt form, wherein the XRPD of the form, obtained from a Cu Kα source, has the characteristic 2θ values of FIG. 9 (Form A).

The disclosure includes a crystalline tebipenem pivoxil malate salt form (Form A), wherein the XRPD of the form, obtained from a Cu Kα source, has any 5, 6, 7, 8, 9, 10, 11, 12 or more of the following values: 9.1, 9.3, 11.0, 11.8, 12.3, 12.9, 13.1, 14.4, 14.9, 15.3, 16.0, 16.6, 17.6, 18.5, 19.0, 19.9, 20.5, 20.8, 21.4, 21.9, 22.2, 23.1, 23.4, 23.9, 24.8, 25.5, 26.0, 26.3, 27.7, or 28.4.

The disclosure includes a crystalline tebipenem pivoxil malate salt form (Form A) characterized by an XRPD diffractogram obtained from a Cu Kα source which comprises peaks at 2θ values of 11.8, 15.3, 17.6, 19.0, and 23.9+/−0.2 degrees 2θ; or 12.9, 18.5, 20.5, 21.9, and 26.3+/−0.2 degrees 2θ.

Figure 11:
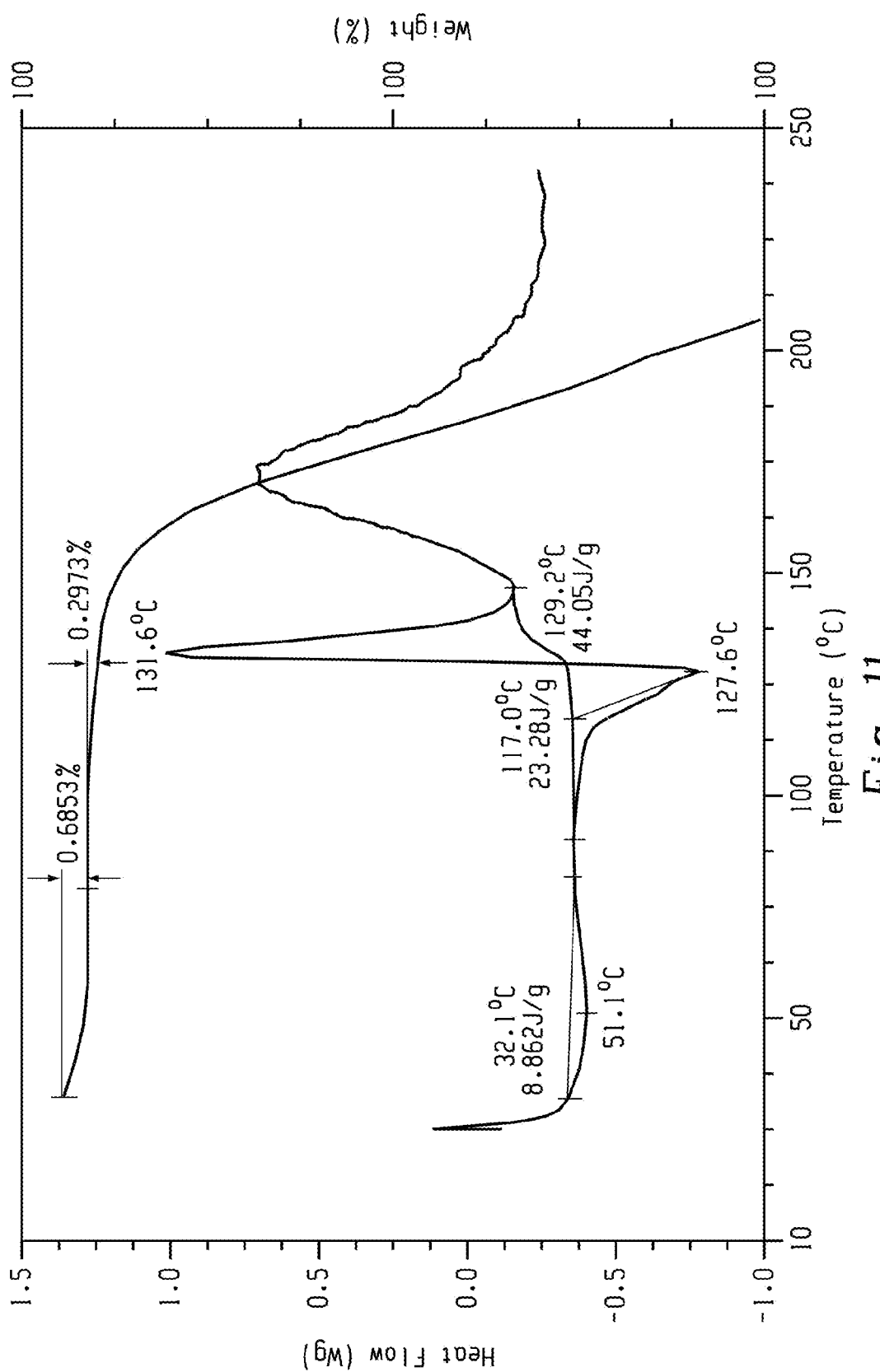
FIG. 11. DSC and TGA profiles of crystalline tebipenem pivoxil malate salt Form A prepared by method 1.

The disclosure includes a crystalline tebipenem pivoxil malate salt Form A, additionally characterized by a DSC profile substantially as shown in FIG. 11.

The disclosure includes crystalline tebipenem pivoxil malate salt Form A additionally characterized by a DSC profile having an endotherm with an onset of 32.1° C. and a minima at 51.1° C. and a second endotherm with an onset of 117° C. and a minima at 127.6° C.

Figure 12:
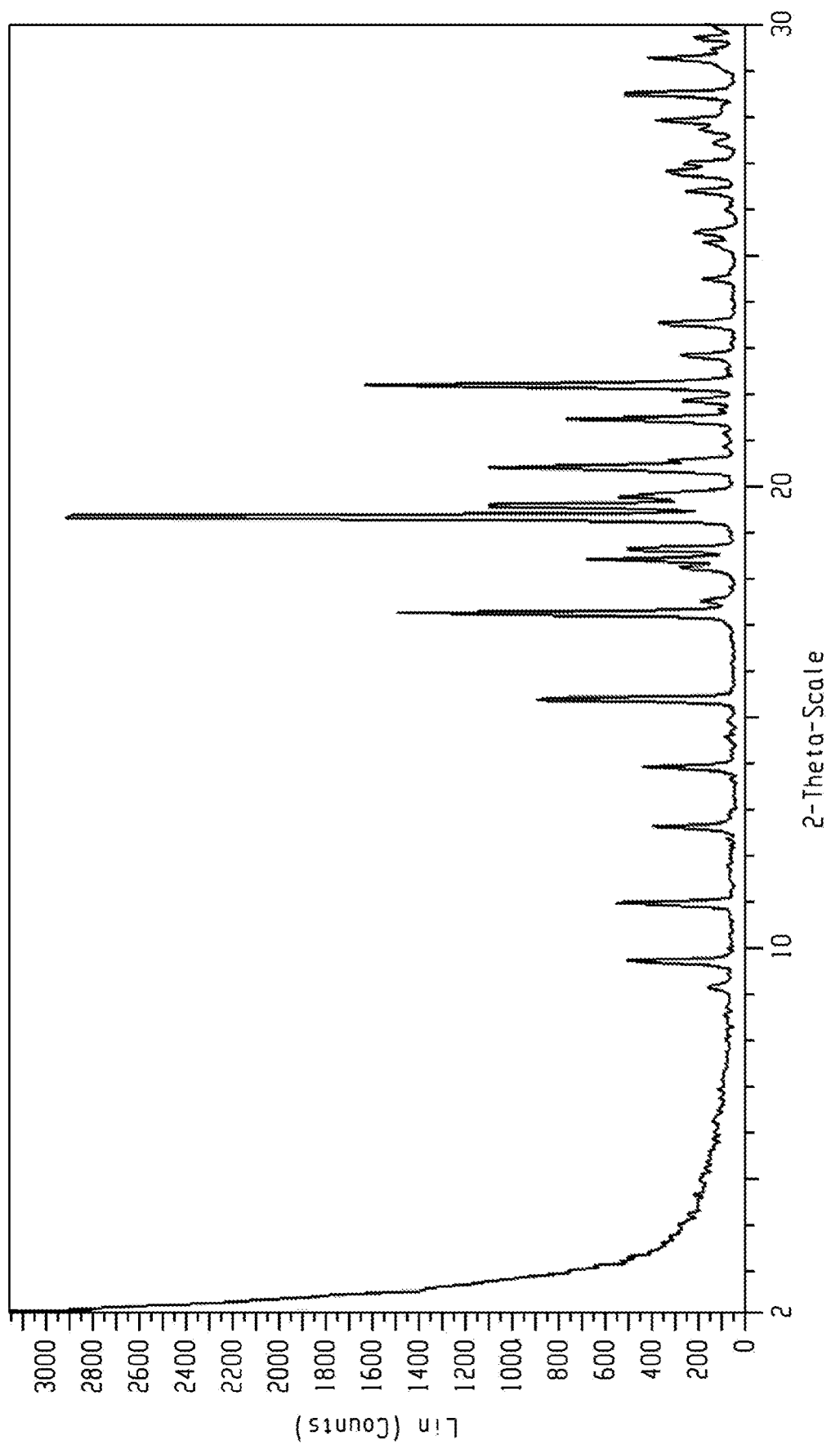
FIG. 12. XRPD diffractogram of crystalline tebipenem pivoxil methane sulfonate salt Form B.

The disclosure includes crystalline tebipenem pivoxil methane sulfonate salt form, wherein the XRPD of the form, obtained from a Cu Kα source, has the characteristic 2θ values of FIG. 12 (Form B).

The disclosure includes a crystalline tebipenem pivoxil methane sulfonate salt form (Form B), wherein the XRPD of the form, obtained from a Cu Kα source, has any 5, 6, 7, 8, 9, 10, 11, 12 or more of the following values: 9.1, 9.6, 10.9, 12.6, 13.9, 14.6, 15.4, 17.2, 17.5, 18.2, 18.4, 18.7, 19.4, 19.6, 19.8, 20.4, 20.6, 21.5, 21.9, 22.2, 22.9, 23.6, 24.5, 25.3, 25.6, 26.4, 26.9, 27.1, 27.5, 27.8, 28.0, 28.6, 29.4, or 29.8.

The disclosure includes a crystalline tebipenem pivoxil methane sulfonate salt form (Form B) characterized by an XRPD diffractogram obtained from a Cu Kα source which comprises peaks at 2θ values of 9.6, 12.6, 15.4, 19.4, and 22.2+/−0.2 degrees 2θ; or 10.9, 13.9, 17.2, 20.4, and 23.6+/−0.2 degrees 2θ.

Figure 13:
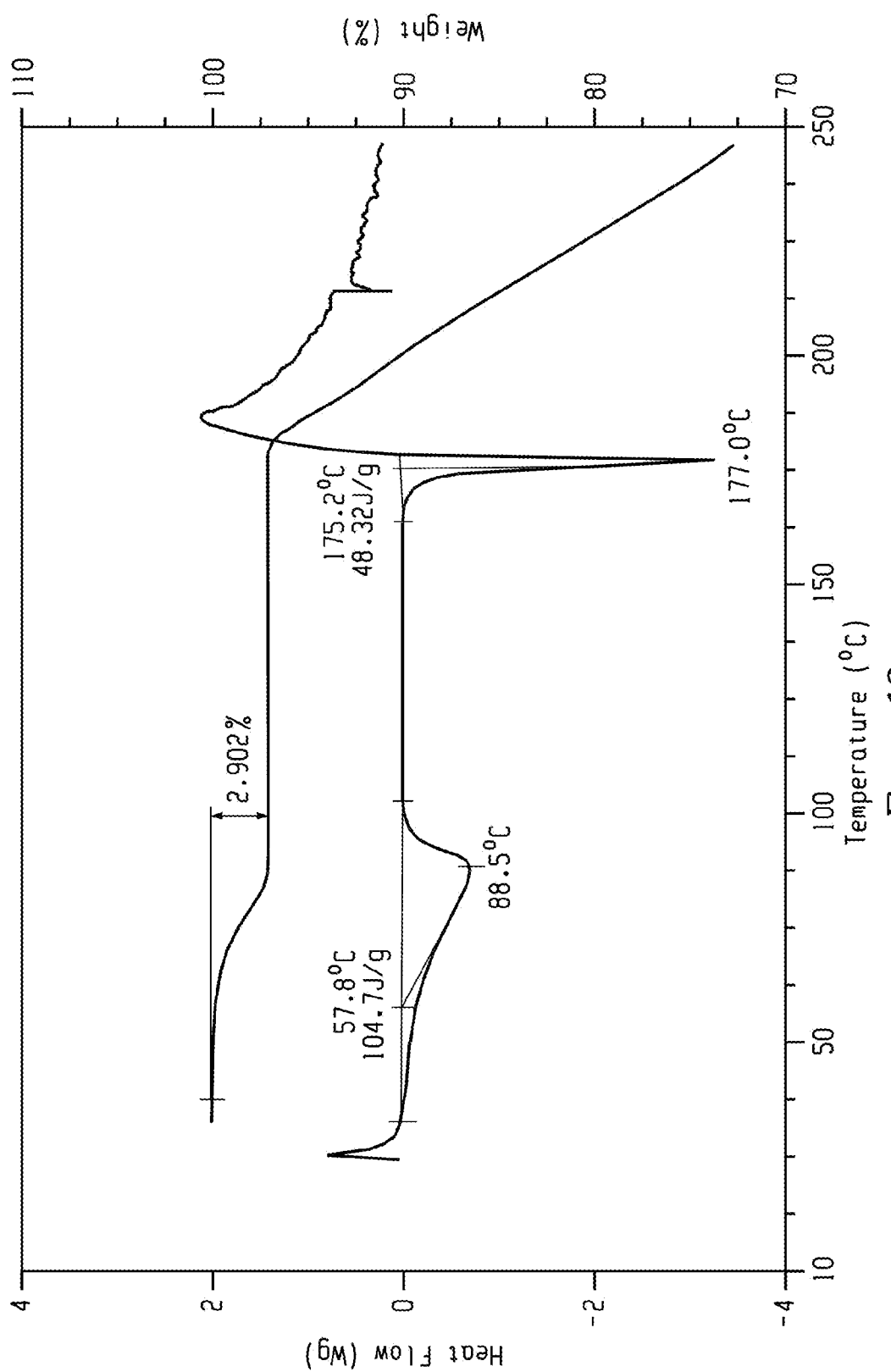
FIG. 13. DSC and TGA profiles of crystalline tebipenem pivoxil methane sulfonate salt Form B.

The disclosure includes a crystalline tebipenem pivoxil methane sulfonate salt of Form B, additionally characterized by a DSC profile substantially as shown in FIG. 13.

The disclosure includes crystalline tebipenem pivoxil methane sulfonate salt Form B, additionally characterized by a DSC profile having an endotherm with an onset of 57.8° C. and a minima at 88.5° C. and a second endotherm with an onset of 175° C. and a minima at 177.0° C.

Figure 14:
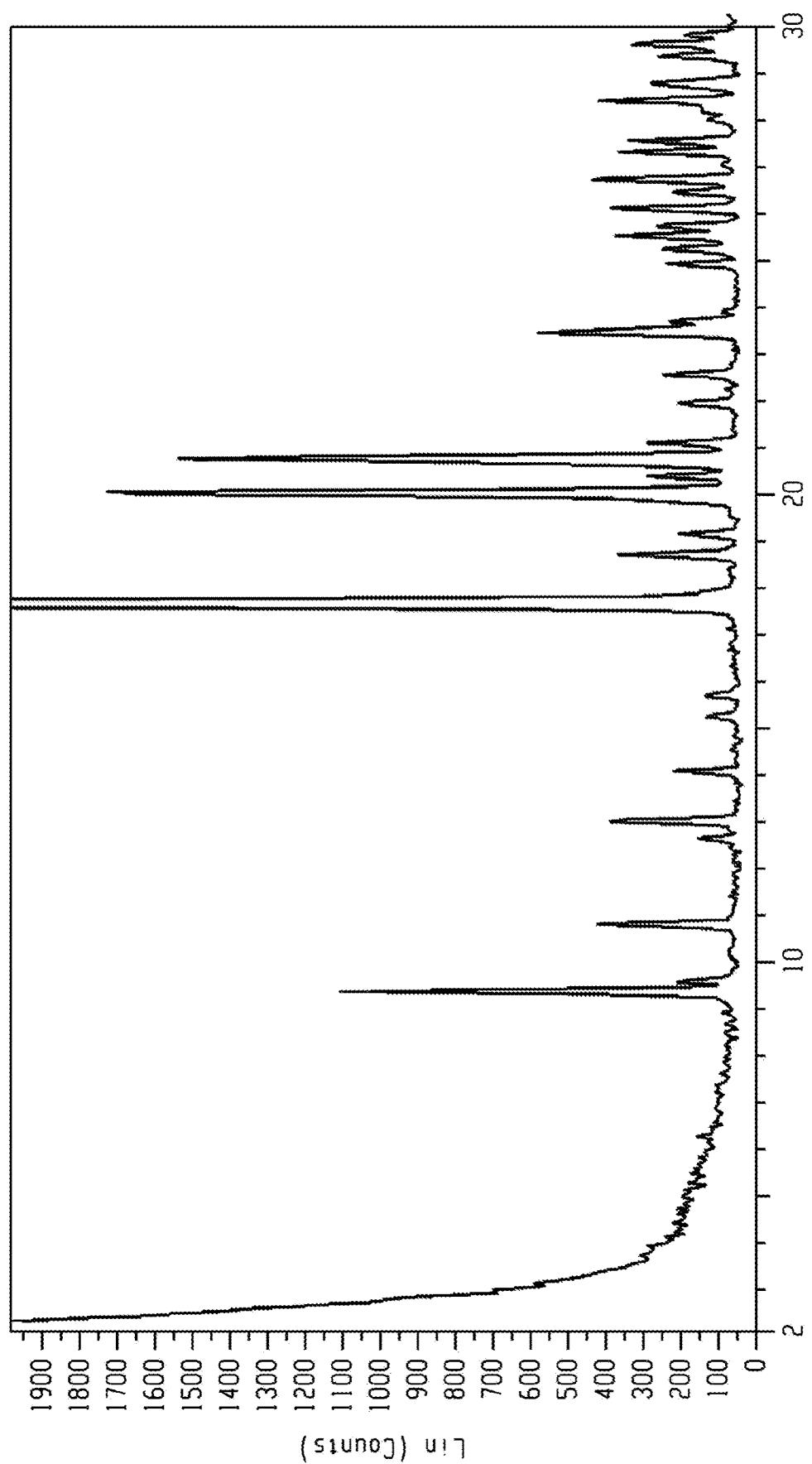
FIG. 14. XRPD diffractogram of crystalline tebipenem pivoxil hydrobromide salt Form B.

The disclosure includes a crystalline tebipenem pivoxil hydrobromide salt form, wherein the XRPD of the form, obtained from a Cu Kα source, has the characteristic 2θ values of FIG. 14 (Form B).

The disclosure includes a crystalline tebipenem pivoxil hydrobromide salt form (Form B), wherein the XRPD of the form, obtained from a Cu Kα source, has any 5, 6, 7, 8, 9, 10, 11, 12 or more of the following values: 9.3, 9.5, 10.7, 12.6, 13.0, 14.0, 15.2, 15.7, 17.6, 18.7, 19.1, 20.0, 20.4, 20.8, 21.1, 21.9, 22.6, 23.5, 23.7, 24.9, 25.3, 25.5, 25.8, 26.1, 26.5, 26.8, 27.3, 27.6, 28.4, 28.8, 29.4, 29.7, or 29.9+/−0.2 degrees 2θ.

The disclosure includes a crystalline tebipenem pivoxil hydrobromide salt form (Form B) characterized by an XRPD diffractogram obtained from a Cu Kα source which comprises peaks at 2θ values of 9.3, 13.0, 17.6, 20.8, and 26.8+/−0.2 degrees 2θ; or 10.7, 14.0, 18.7, 20.0, and 23.5+/−0.2 degrees 2θ.

Figure 15:
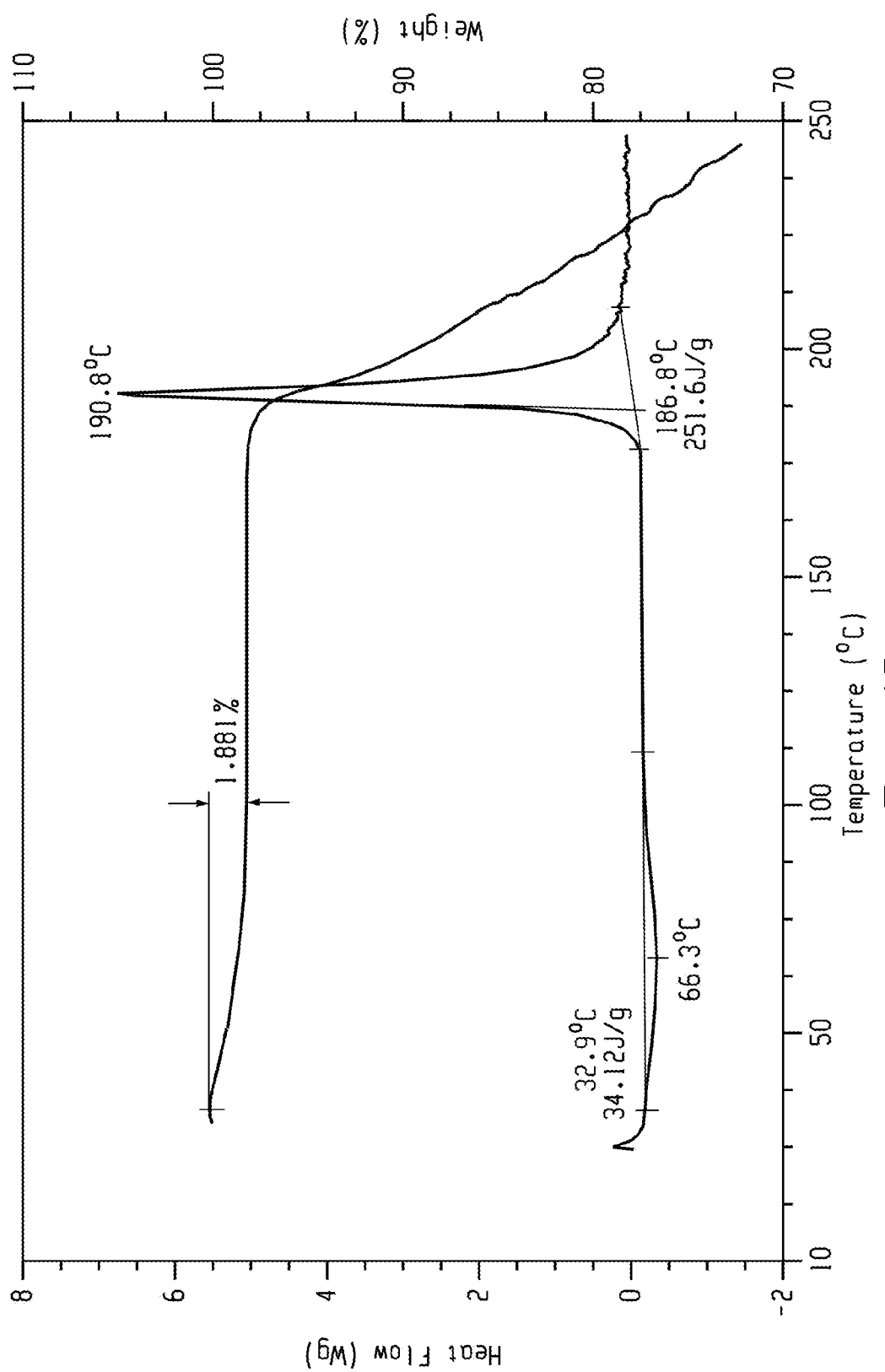
FIG. 15. DSC and TGA profiles of crystalline tebipenem pivoxil hydrobromide salt Form B.

The disclosure includes a crystalline includes tebipenem pivoxil hydrobromide salt Form B additionally characterized by a DSC profile substantially as shown in FIG. 15.

The disclosure includes crystalline tebipenem pivoxil hydrobromide salt Form B additionally characterized by a DSC profile having an endotherm with an onset of 32.9° C. and a minima at 66.3° C. and a second endotherm with an onset of 186.8° C. and a maxima at 190.8° C.

Figure 16:
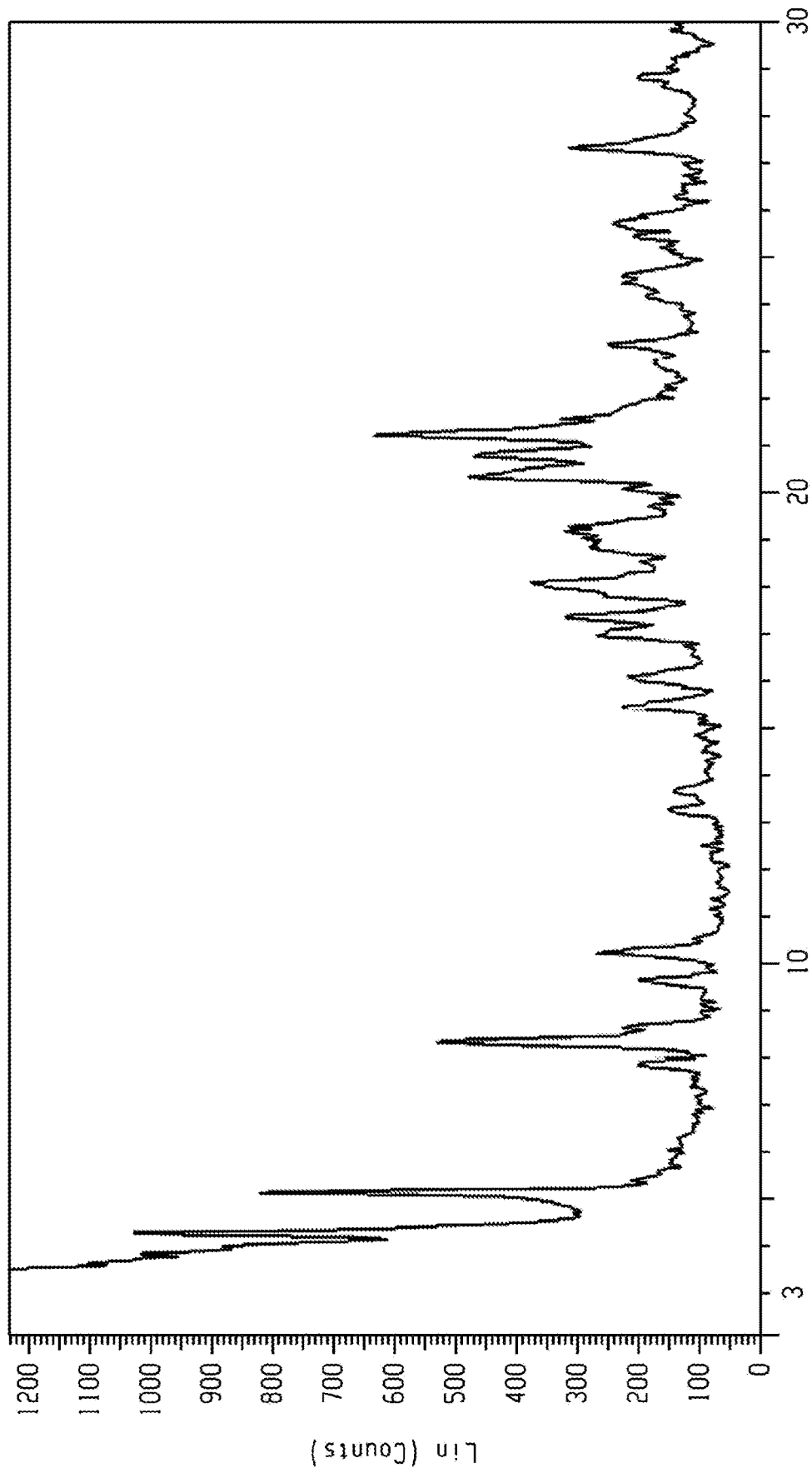
FIG. 16. XRPD diffractogram of crystalline tebipenem pivoxil edisylate salt Form A.

The disclosure includes a crystalline tebipenem pivoxil edisylate salt form, wherein the form, obtained from a Cu Kα source, has the characteristic 2θ values of FIG. 16.

The disclosure includes a crystalline tebipenem pivoxil edisylate salt form (Form A), wherein the XRPD of the form, obtained from a Cu Kα source, has any 5, 6, 7, 8, 9, 10, 11, 12 or more of the following values: 4.1, 5.0, 7.7, 8.2, 8.5, 9.5, 10.1, 13.1, 13.5, 15.4, 16, 16.9, 17.3, 18, 19.1, 20.3, 20.7, 21.2, 22.7, 23.1, 24.5, 25.7, 27.3, 28.8+/−0.2 degrees 2θ.

A crystalline tebipenem pivoxil edisylate salt form (Form A) characterized by an XRPD diffractogram obtained from a Cu Kα source which comprises peaks at 2θ values of 4.1, 8.2, 10.1, 20.3, and 21.2+/−0.2 degrees 2θ; or 5.0, 10.1, 15.4, 18.0, and 20.7+/−0.2 degrees 2θ.

Figure 17:
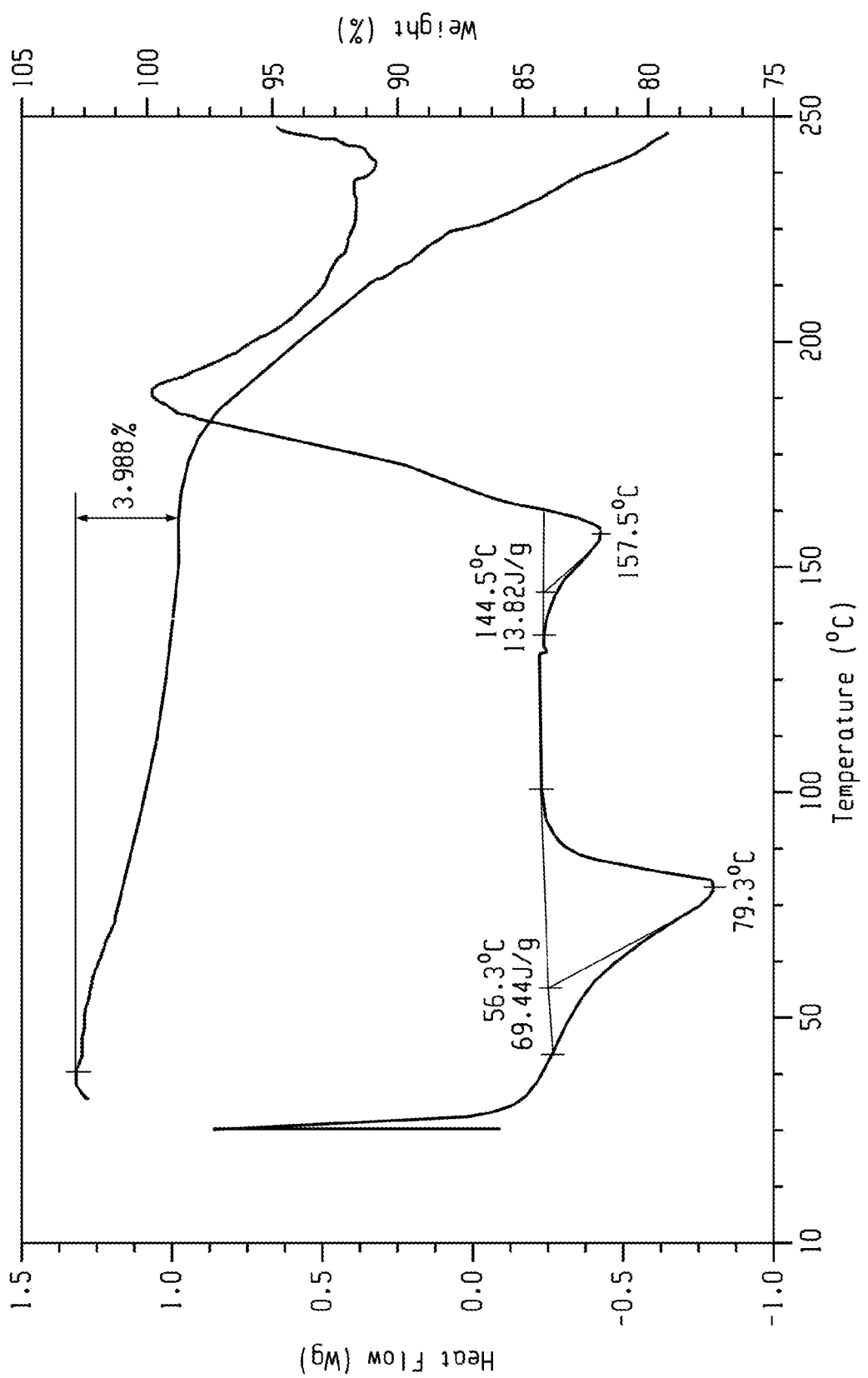
FIG. 17. DSC and TGA profiles of crystalline tebipenem pivoxil edisylate salt Form A.

The disclosure includes crystalline tebipenem pivoxil edisylate salt Form A characterized by a DSC profile substantially as shown in FIG. 17.

The disclosure includes a crystalline tebipenem pivoxil edisylate salt form (Form A) characterized by a DSC profile having an endotherm with an onset of 56.3° C. and a minima at 79.3° C. and a second endotherm with an onset of 144.5° C. and a minima at 157.5° C.

The disclosure includes a crystalline tebipenem pivoxil salt form of any one of FIG. 1, 3, 5, 7, 9, 10, 12, 14, 16, 21, or 23 wherein the crystalline tebipenem pivoxil salt form is at least 90%, 95%, 97%, 98%, 99% ot 99.5% pure.

The disclosure includes a pharmaceutical composition comprising a tebipenem pivoxil salt and a physiologically acceptable carrier, wherein the tebipenem pivoxil salt comprises at least 90%, 95%, 97%, 98%, 99% ot 99.5% of a crystalline tebipenem pivoxil salt of FIG. 1, 3, 5, 7, 9, 10, 12, 14, 16, 21, or 23. The pharmaceutical composition can be an intraarterial, intravenous, injectable, topical, mucosal, parenteral (including subcutaneous, intramuscular, or bolus injection), sublingual, transdermal, buccal, or oral dosage form. The composition can be an oral dosage form, for example, in the form of a tablet or capsule.

In some embodiments, pharmaceutical compositions and dosage forms provided herein include one or more crystalline forms including a tebipenem pivoxil salt.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of bacterial infection or a related disorder may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

Lactose-free compositions of the invention can comprise excipients that are well known in the art and are listed, for example, in the U.S. Pharmocopia (USP) SP (XXI)/NF (XVI). In general, lactose-free compositions comprise an active ingredient, a binder/filler, and a lubricant in pharmaceutically compatible and pharmaceutically acceptable amounts. Preferred lactose-free dosage forms comprise an active ingredient, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles &Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms provided herein lie within the range of from about 1 mg to about 1,000 mg per day, given as a single once-a-day dose in the morning but preferably as divided doses throughout the day. More specifically, the daily dose is administered twice daily in equally divided doses. Specifically, a daily dose range may be from about 5 mg to about 500 mg per day, more specifically, between about 10 mg and about 200 mg per day. In managing the patient, the therapy may be initiated at a lower dose, perhaps about 1 mg to about 25 mg, and increased if necessary up to about 200 mg to about 1,000 mg per day as either a single dose or divided doses, depending on the patient's global response.

Oral dosage forms. Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally *Remington's Pharmaceutical Sciences*, 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101 ™, AVICEL-PH-103™, AVICEL RC-581™, AVICEL-PH105™ (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581™. Suitable anhydrous or low moisture excipients or additives include AVICEL-PH-103™ and Starch 1500 LM™.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200™, manufactured by W.R. Grace Co. of Baltimore, Md.), a coagulated aerosol of synthetic silica (marketed by Degussa Co. of Plano, Tex.), CAB-O-SIL™ (a pyrogenic silicon dioxide product sold by Cabot Co. of Boston, Mass.), and mixtures thereof. If used at all, lubricants are typically used in an amount of less than about one weight percent of the pharmaceutical compositions or dosage forms into which they are incorporated.

Delayed Release Dosage Forms. Crystalline forms comprising a tebipenem pivoxil salt as provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms. Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal, Topical, and Mucosal Dosage Forms. Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences*, 16th and 18th eds., Mack Publishing, Easton Pa. (1980 & 1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80™ (polysorbate 80) and Span 60™ (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different crystalline forms comprising the active ingredients can be used to further adjust the properties of the resulting composition.

Kits. This invention encompasses kits which, when used by the medical practitioner, can simplify the administration of appropriate amounts of active ingredients to a patient.

A typical kit of the invention comprises a unit dosage form of a tebipenem pivoxil salt, or a pharmaceutically acceptable crystalline form or prodrug thereof, and a unit dosage form of a second active ingredient. Examples of second active ingredients include, but are not limited to, those listed herein.

Kits of the invention can further comprise devices that are used to administer the active ingredient(s). Examples of such devices include, but are not limited to, syringes, drip bags, patches, and inhalers.

Kits of the invention can further comprise pharmaceutically acceptable vehicles that can be used to administer one or more active ingredients. For example, if an active ingredient is provided in a crystalline form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

The disclosure includes a method for treating a bacterial infection, comprising administering to a patient in need of such treatment a therapeutically effective amount of a pharmaceutical composition containing a crystalline tebipenem pivoxil salt of FIG. 1, 3, 5, 7, 9, 10, 12, 14, or 16. The method can include administering a crystalline tebipenem pivoxil salt, wherein the composition contains an active agent in addition to the crystalline tebipenem pivoxil salt. The method can include administering the crystalline tebipenem pivoxil salt to the patient in combination with an active agent. The active agent can be an antibiotic. The bacterial infection can a Gram negative bacterial infection such as an *E. coli* infection, a *Klebsiella pneumoniae* infection, an *Acinetobacter baumannii* infection, a *Pseudomonas aeruginosa*, a *Neisseria gonorrhoeae* infection, or a *Yersinia pestis* infection.

Specific methods of the invention can comprise the administration of an additional therapeutic agent such as, but not limited to, anti-inflammatory drugs, antihistamines and decongestants. Examples of such additional therapeutic agents include, but are not limited to: antihistamines including, but not limited to, ethanolamines, ethylenediamines, piperazines, and phenothiazines; antiinflammatory drugs; NSAIDS, including, but not limited to, aspirin, salicylates, acetominophen, indomethacin, sulindac, etodolac, fenamates, tolmetin, ketorolac, diclofenac, ibuprofen, naproxen, fenoprofen, ketoprofen, flurbiprofen, oxaprozin, piroxicam, meloxicam, pyrazolon derivatives; and steroids including, but not limited to, cortical steroids and adrenocortical steroids.

As stated above, certain crystalline forms comprising a tebipenem pivoxil salt may be used in the treatment or prevention of a wide range of bacterial infections. The magnitude of a prophylactic or therapeutic dose of a particular active ingredient of the invention in the acute or chronic management of a disease or condition may vary with the nature and severity of the disease or condition and the route by which the active ingredient is administered. The dose, and perhaps the dose frequency, will also vary according to the age, body weight, and response of the individual patient. Suitable dosing regimens can be readily selected by those skilled in the art with due consideration of such factors. In general, the recommended daily dose range for the conditions described herein lie within the range of from about 1 mg to about 1,000 mg per day, given as a single once-a-day dose preferably as divided doses throughout a day. More specifically, the daily dose is administered twice daily in equally divided doses. Specifically, a daily dose range may be from about 5 mg to about 500 mg per day, more specifically, between about 10 mg and about 200 mg per day. Specifically, the daily dose may be administered in 5 mg, 10 mg, 15 mg, 20 mg, 25 mg, 50 mg, or 100 mg dosage forms. In managing the patient, the therapy should be initiated at a lower dose, perhaps about 1 mg to about 25 mg, and increased if necessary up to about 200 mg to about 1,000 mg per day as either a single dose or divided doses, depending on the patient's global response. Alternatively, the daily dose is from 0.01 mg/kg to 100 mg/kg.

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

As stated above, the pharmaceutical composition of the disclosure may also contain a pharmaceutically acceptable carrier, which can be any pharmaceutically acceptable excipient such as a binder, filler, lubricant, solvent, disintegrant or coating. Examples of pharmaceutically acceptable carrier are provided above.

The crystalline tebipenem pivoxil salt is generally present within a pharmaceutical composition in a therapeutically effective amount. As used herein, a "therapeutically effective amount" (or dose) is an amount that, upon administration to a patient, results in a discernible patient benefit. It will be apparent that the therapeutically effective amount will depend upon the particular patient, the indication for which it is administered, as well as the effects of any co-administered drugs.

As also stated above, in an embodiment the composition may be suitable for pharmaceutical use and may be in the form of a pharmaceutical composition. The pharmaceutical composition may have any suitable form, and may be a tablet, capsule, solution, suspension, or a combination thereof.

The pharmaceutical composition may be used to treat a disorder, e.g., a bacterial infection. Therapeutic methods provided herein may be used to treat an existing disorder, or to prevent, decrease the severity of, or delay the onset of a disorder in a patient. Alternatively, or in addition, compounds provided herein may be administered to a patient to prevent infection in a healthy patient. Patients include humans, domesticated companion animals (pets, e.g., dogs) and livestock animals. A method for treating a disorder may comprise administering to a patient in need of treatment a therapeutically effective amount of the pharmaceutical composition.

Pharmaceutical compositions may be packaged or used for the manufacture of a medicament for treatment. Packaged pharmaceutical preparations include a container holding a therapeutically effective amount of the crystalline tebipenem pivoxil salt and may further include labeling (e.g., instructions) indicating that the contained composition is to be used for treating the disorder.

This disclosure is further illustrated by the following examples that should not be construed as limiting.

EXAMPLES

Instrumental Techniques

The following instrumental techniques are used for analysis of all crystal forms unless otherwise noted.

X-Ray Powder Diffraction (XRPD)

X-Ray Powder Diffraction patterns were collected on a Bruker D8 diffractometer using Cu Kα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.6.1 and the data were analysed and presented using Diffrac Plus EVA v15.0.0.0. Samples were run under ambient conditions as flat plate specimens using powder as received. The sample was gently packed into a cavity cut into polished, zero-background (510) silicon wafer. The sample was rotated in its own plane during analysis. The details of the data collection are: Angular range: 2 to 42° 2θ, step size: 0.05° 2θ and collection time: 0.5 s/step.

Differential Scanning Calorimetry (DSC)

DSC was conducted with a TA Instruments Q100 differential scanning calorimeter equipped with an autosampler and a refrigerated cooling system under 40 mL/min $N_2$ purge. DSC thermograms were obtained at 5° C./min in crimped Al pans.

DSC data were also collected on a TA Instruments Q2000 equipped with a 50 position auto-sampler. The calibration for thermal capacity was carried out using sapphire and the calibration for energy and temperature was carried out using certified indium. Typically 0.5-3 mg of each sample, in a pin-holed aluminium pan, was heated at 10° C./min from 25° C. to 300° C. A purge of dry nitrogen at 50 ml/min was maintained over the sample.

Thermogravimetric Analysis (TGA)

TGA thermograms were obtained with a TA Instruments Q500 thermogravimetric analyzer, equipped with a 16 position auto-sampler, under 40 mL/min $N_2$ purge at 5° C./min in Pt or Al pans. The instrument was temperature calibrated using certified alumel and nickel. Typically 5-10 mg of each sample was loaded onto a pre-tared aluminium DSC pan and heated at 10° C./min from ambient temperature to 300° C. A nitrogen purge at 60 ml/min was maintained over the sample.

High Pressure Liquid Chromatography (HPLC)

Purity analysis was performed on an Agilent HP1100 series system equipped with a diode array detector and using ChemStation software vB.04.03 using the Method A of Method B as detailed below.

TABLE A

HPLC Method A for chemical purity determinations

| Parameter | Value | | |
|---|---|---|---|
| Type of method | Reverse phase with gradient elution | | |
| Sample Preparation | 0.5 mg/ml in acetonitrile | | |
| Column | Supelco Ascentis Express C18, 100 x 4.6 mm, 2.7 μm | | |
| Column Temperature (° C.) | 25 | | |
| Injection (l) | 3 or 5 | | |
| Wavelength, Bandwidth (nm) | 255, 90 | | |
| Flow Rate (ml/min) | 2 | | |
| Phase A | 0.1% TFA in water | | |
| Phase B | 0.085% TFA in acetonitrile | | |
| Timetable | Time | % Phase | % Phase |
| | (min) | A | B |
| | 0 | 95 | 5 |
| | 6 | 5 | 95 |
| | 6.2 | 95 | 5 |
| | 8 | 95 | 5 |

HPLC analysis was performed according to Method B on an Agilent HP1100/1200 system equipped with a diode array detector and using Chemstation software. The analysis was conducted by using a reverse phase column Agilent LiChrospher 100 RP-18, 5 μm, 250×4 mm under isocratic conditions at ambient temperature. Before injection, the sample concentration was approximately 0.5 mg/mL in 1:1 acetonitrile-water mixture (volume to volume), and the injection size was 10 μL. The mobile phase was 68/30/2(volume/volume/volume) 50 mM ammonium acetate in water/acetonitrile/triethylamine, pH was adjusted to 3.5 with concentrated phosphoric acid. The flow rate was 0.8 mL/min, and the run time was 15 minutes. The detection took place at 330 nm wavelength.

Proton Nuclear Magnetic Resonance ($^1$H NMR)

NMR spectra were collected on a Bruker 400 MHz instrument equipped with an auto-sampler and controlled by a DRX400 console. Automated experiments were acquired using ICON-NMR v4.0.7 running with Topspin v1.3 using the standard Bruker loaded experiments. Samples were prepared at a concentration of 2-5 mg/mL by dissolution in DMSO-d6 solvent. Off-line analysis was carried out using ACD Spectrus Processor 2014.

Comparative Example 1. Crystalline Form of Tebipenem Pivoxil

Figure 18:
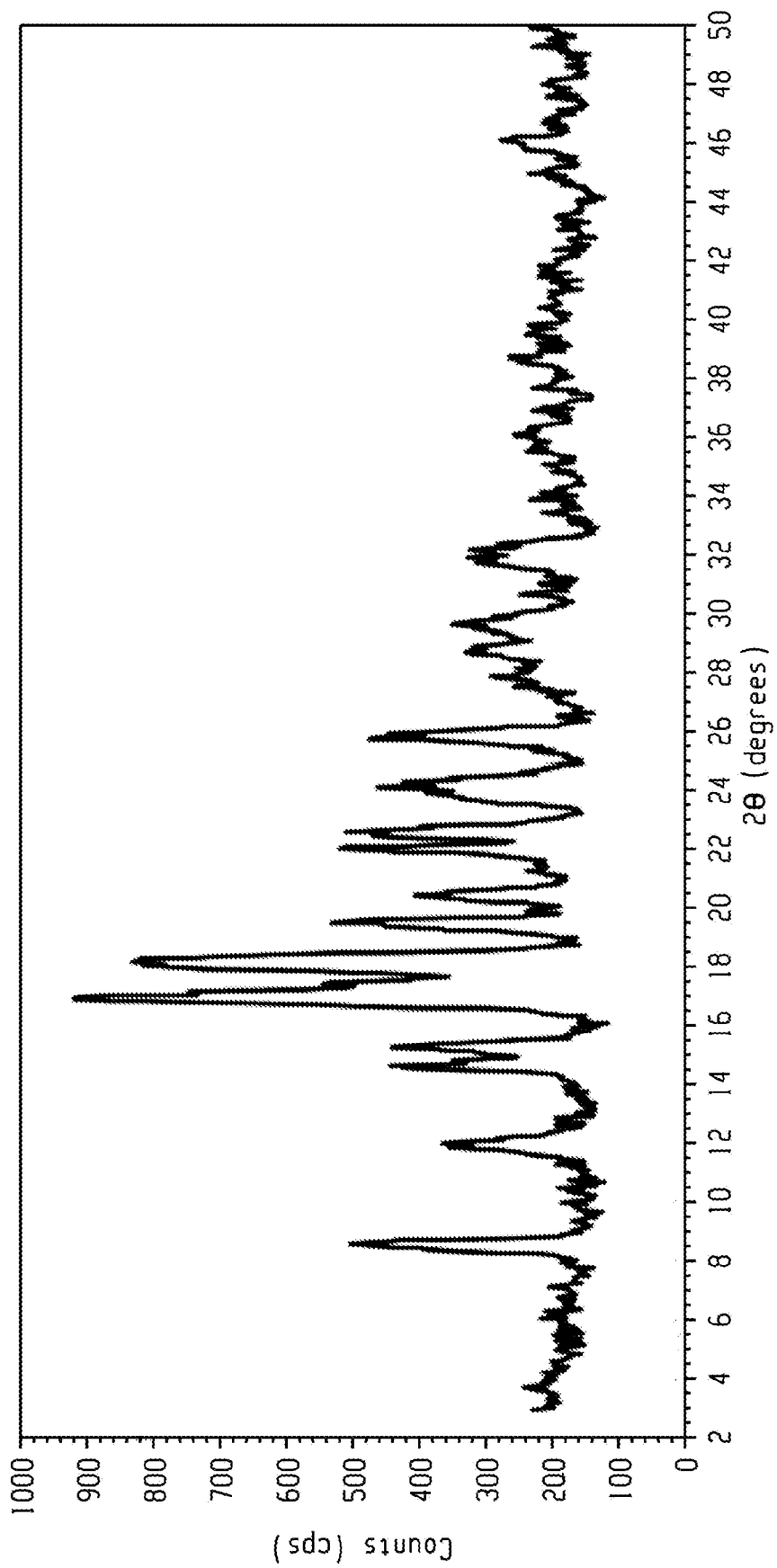
FIG. 18. XRPD diffractogram of crystalline tebipenem pivoxil free base.

Crystalline tebipenem pivoxil Form A was prepared according to known methods. An XRPD diffractogram of crystalline tebipenem pivoxil was obtained (FIG. 18). The crystalline tebipenem pivoxil XRPD diffractogram exhibited the peaks listed in Table 1.

TABLE 1

Characteristic angles of Tebipenem Pivoxil (2θ) Form A

| Characteristic angle (°) | Relative intensity (%) |
| --- | --- |
| 9.55 | 29.12 |
| 11.00 | 25.06 |
| 12.80 | 23.14 |
| 13.25 | 21.78 |
| 15.40 | 20.77 |
| 17.95 | 100.00 |
| 19.20 | 20.32 |
| 20.35 | 51.69 |
| 21.10 | 64.79 |
| 23.85 | 33.18 |
| 25.80 | 21.78 |
| 26.40 | 20.65 |
| 27.75 | 23.36 |
| 28.75 | 24.27 |
| 37.50 | 25.62 |

DSC data (now shown) of crystalline tebipenem pivoxil shows a sharp endotherm at 132.1° C. followed by two distinct exotherms at 161.8 and 175.9° C. TGA showed gradual degradation beginning at about 109.5° C. and rapid degradation after 169.2° C. Crystalline tebipenem pivoxil exhibited approximately 2% weight loss between 109.5° C. and 169.2° C.

$^1$H NMR (400 MHz, DMSO-$d_6$) δ ppm 1.07-1.16 (m, 15H) 1.19 (s, 1H) 1.98-1.99 (m, 1H) 2.73 (s, 1H) 2.89 (s, 1H) 3.07 (s, 1H) 3.24 (dd, J=6.25, 2.59 Hz, 1H) 3.27-3.27 (m, 1H) 3.31-3.38 (m, 3H) 3.73 (td, J=6.79, 3.60 Hz, 2H) 3.87 (t, J=7.58 Hz, 2H) 3.91-4.01 (m, 1H) 4.03 (d, J=7.07 Hz, 1H) 4.18 (dd, J=9.35, 2.65 Hz, 1H) 4.27-4.39 (m, 3H) 5.09 (d, J=5.18 Hz, 1H) 5.74 (d, J=5.94 Hz, 1H) 5.89 (d, J=5.94 Hz, 1H) 7.95 (s, 1H).

Figure 19:
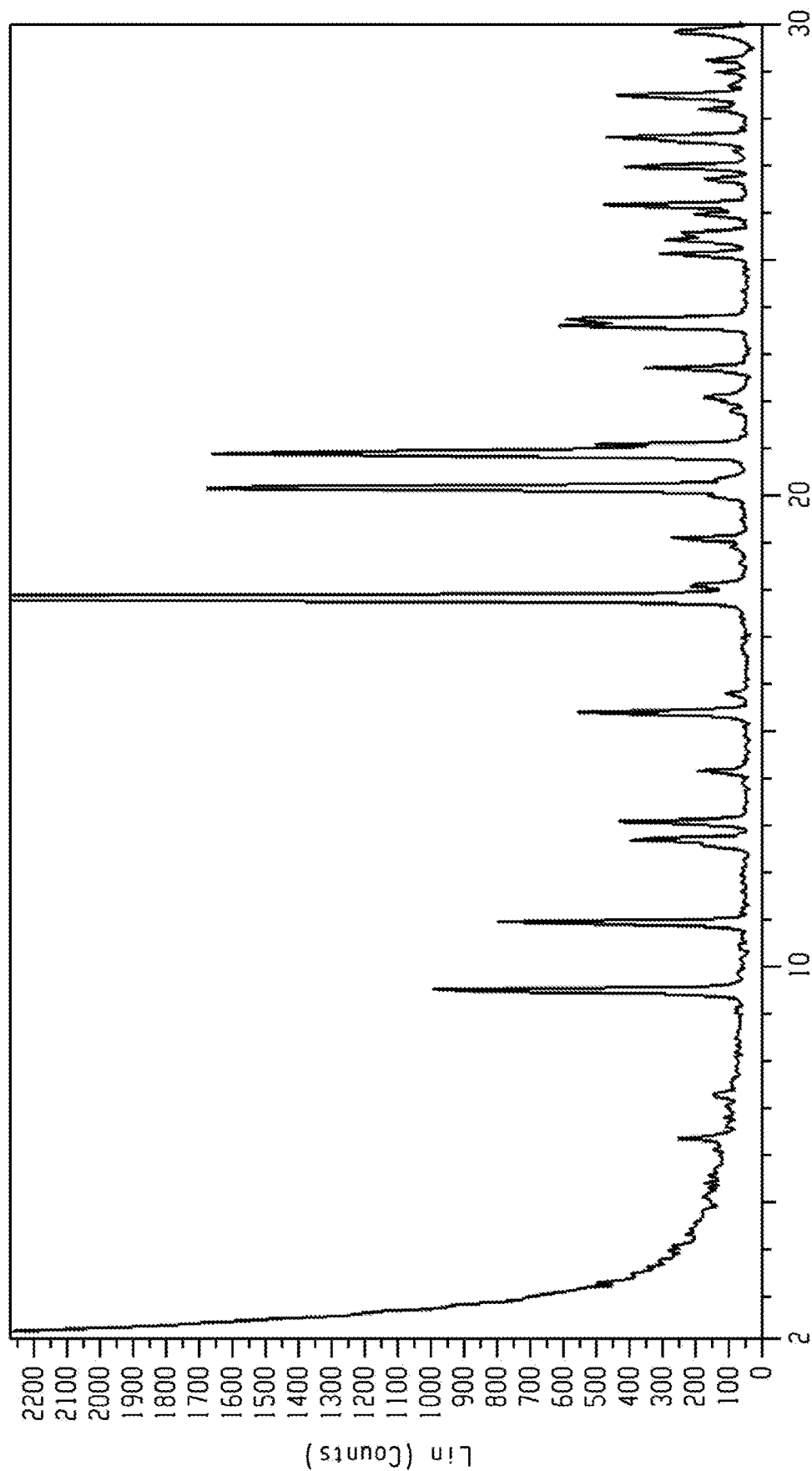
FIG. 19. XRPD diffractogram of crystalline tebipenem pivoxil hydrochloride salt Form A.

Comparative Example 2. Crystalline Tebipenem Pivoxil Hydrochloride (HCL) Salt Form A Tebipenem pivoxil (35 mg) was dissolved in MeCN (270 μL). The acid stock solution (1 M HCl in THF) was then added to 1 mol eq. and stirred at 25° C., 500 rpm using a magnetic stir bar in a Polar Bear device for 20 minutes. The sample was then cooled to 0° C. over a 2 hour period (0.2° C./min) and maintained at 0° C. for about 2 hours. The suspension obtained was filtered using a fritted filter and air-dried on a filter block at ambient for 15 minutes. This sample was found to be 99.5% pure by HPLC (Method A). The XRPD diffractogram for this crystalline form is provided in FIG. 19 and the peak listing appears in Table 2.

Crystalline tebipenem pivoxil HCl salt of the same form was also obtained at equivalent purity using the method in the preceding paragraph with the following changes. Tebipenem pivoxil was dissolved in EtOH (930 μL). The acid stock solution (1 M HCl in THF) was then added to 1 mol eq. and stirred at 25° C., 500 rpm using a magnetic stir bar in a Polar Bear device for 20 minutes. The sample was then cooled to 5° C. over 2 hours (0.2° C./min) and maintained at 5° C. for about 2 hours.

TABLE 2

Characteristic angles (2θ) of Tebipenem Pivoxil Hydrochloride Salt Form A

| Characteristic angle (°) | Relative intensity (%) |
| --- | --- |
| 6.2 | 4.6 |
| 7.2 | 2.8 |
| 9.4 | 17.5 |
| 10.9 | 14.1 |
| 12.5 | 3.5 |
| 12.6 | 7.1 |
| 13 | 7.8 |
| 14.1 | 3.7 |
| 15.4 | 9.9 |
| 15.8 | 2.3 |
| 17.9 | 100 |
| 18.1 | 4.1 |
| 19.1 | 4.8 |
| 20.2 | 29.4 |
| 20.9 | 29.1 |
| 21.1 | 9.2 |
| 21.9 | 1.9 |
| 22.1 | 3.4 |
| 22.8 | 6.1 |
| 23.7 | 12.8 |
| 23.8 | 10.5 |
| 25.2 | 5.6 |
| 25.5 | 7.1 |
| 25.7 | 4.7 |
| 26.1 | 3.9 |
| 26.3 | 8.5 |
| 26.8 | 3.3 |
| 27.1 | 7.5 |
| 27.7 | 8.4 |
| 28.3 | 3.6 |
| 28.6 | 8.1 |
| 29.1 | 2.7 |
| 29.4 | 3.3 |
| 30 | 5 |

Figure 20:
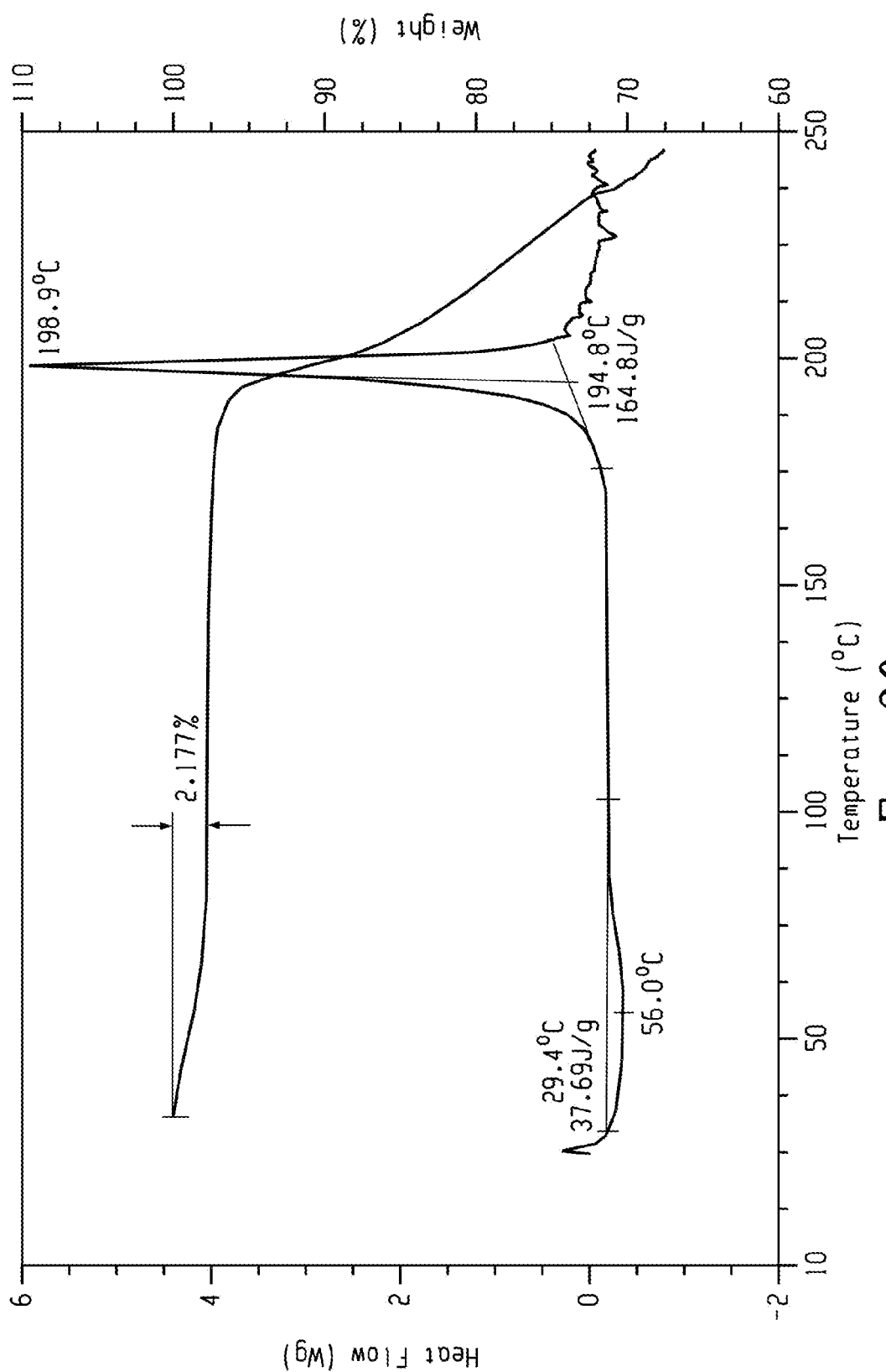
FIG. 20. DSC and TGA profiles of tebipenem pivoxil hydrochloride salt Form A.
Figure 21:
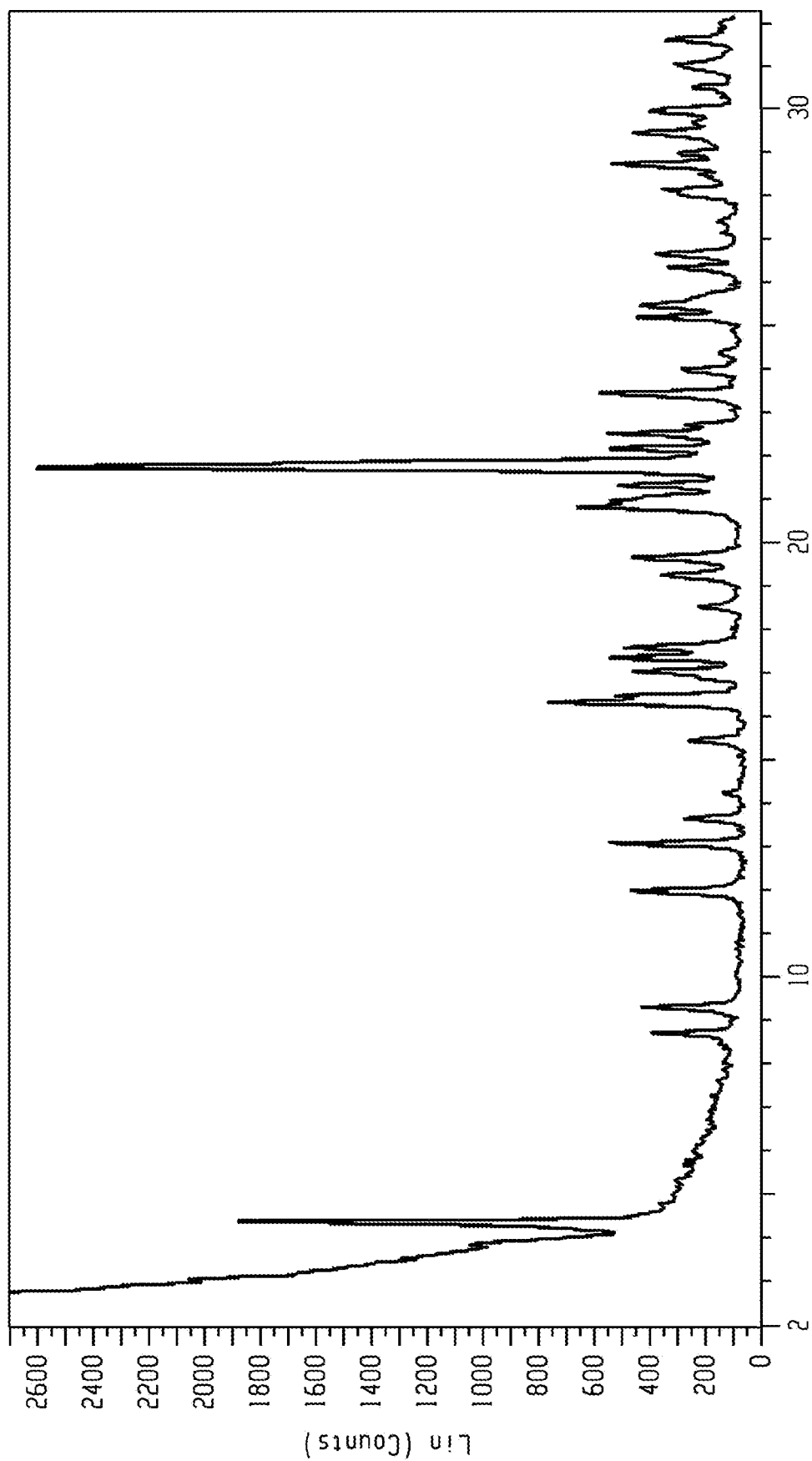
FIG. 21. XRPD diffractogram of crystalline tebipenem pivoxil hydrobromide salt Form C.

The DSC profile for crystalline tebipenem pivoxil (FIG. 20) hydrochloride salt Form A shows a broad endotherm having an onset of 29.4° C. with a minima at 56° C. and an enthalpy of fusion of 38 J/g. The DSC also shows an exotherm at the onset of degradation at 194.8° C.

TGA (also shown in FIG. 17) showed at 2.2% weight loss from room temperature to 100° C. No other thermal events were recorded until the onset of degradation at about 150° C.

$^1$H NMR (400 MHz, DMSO-$d_6$) δ ppm 1.05-1.18 (m, 15H) 2.08 (s, 1H) 3.28 (dd, J=6.19, 2.65 Hz, 1H) 3.30-3.41 (m, 2H) 3.42-3.42 (m, 1H) 3.61-3.68 (m, 2H) 3.89-4.01 (m, 3H) 4.14-4.27 (m, 3H) 4.40-4.50 (m, 1H) 4.69-4.81 (m, 2H) 5.14 (br s, 1H) 5.75 (d, J=5.94 Hz, 1H) 5.88 (d, J=5.94 Hz, 1H) 10.46 (s, 1H). $^1$H NMR and HPLC were repeated 1 week post storage at 40° C./75% relative humidity. Tebipenem pivoxil hydrochloride salt crystalline form A was obtained and determined to be 98.9% pure by HPLC.

Example 1. Crystalline Tebipenem Pivoxil Ethane Sulfonate (ESA) Salt

Tebipenem pivoxil (35 mg) was dissolved in MeCN (270 μL), then the acid stock solution (1 M ethane sulfonic acid in THF) was added to 1 mol eq. and stirred at 25° C., 500 rpm using a magnetic stir bar in a Polar Bear device (Cambridge Reactor Design for 20 minutes. The sample was then cooled to 0° C. over a 2 hour period (0.2° C./min) and then maintained at 0° C. for ~2 hours. No precipitation was observed. The sample was then cooled by 0.5° C./min to −15° C. at 0.5° C./min and stored at −20° C. for 2 days. The solution was transferred to a 20 mL scintillation vial and antisolvent (tert-methyl butyl ether, TBME) was added slowly whilst stirring at 25° C., 500 rpm until a precipitate formed at a ratio of 10:1 antisolvent:solvent (v/v). The suspension obtained was filtered using a fritted filter and air-dried on a filter block at ambient for 15 minutes.

The XRPD spectra for crystalline tebipenem pivoxil ethane sulfonate Form A is shown in FIG. 1. The XRPD diffractogram for this crystalline form exhibited the characteristic peaks listed in Table 3. The sample of tebipenem pivoxil ethane sulfonate (esylate) salt crystalline Form A was determined to be 98.9% pure by HPLC, Method A.

XRPD and HPLC analysis were performed again after one week of storage at 40° C., 75% relative humidity. The XRPD spectra was substantially unchanged, however the sample was found to have a substantially lower purity of be 80.7% by HPLC Method A.

TABLE 3

Characteristic angles (2θ) of Tebipenem Pivoxil Ethane Sulfonate Salt Form A

| Characteristic angle (°) | Relative intensity (%) |
| --- | --- |
| 5.7 | 23.7 |
| 8.8 | 12.8 |
| 9.6 | 29.5 |
| 10.8 | 45.5 |
| 12.4 | 29.8 |
| 13.7 | 32.5 |
| 15.1 | 84.4 |
| 16.9 | 87.1 |
| 17.8 | 23 |
| 18.4 | 29.8 |
| 18.7 | 41.6 |
| 19.0 | 100 |
| 19.3 | 46.1 |
| 20.0 | 22 |
| 20.3 | 55.5 |
| 21.0 | 40 |
| 21.8 | 23.6 |
| 22.1 | 89.5 |
| 22.4 | 14.9 |
| 23.0 | 29.4 |
| 23.4 | 16.4 |
| 24.9 | 11.8 |
| 25.2 | 16.4 |
| 25.9 | 30 |
| 26.2 | 17.1 |
| 26.5 | 19.1 |
| 26.8 | 19.1 |
| 27.2 | 17 |
| 27.9 | 48.7 |
| 28.6 | 15.8 |
| 29.2 | 16.3 |
| 29.7 | 16.5 |

The DSC profile for crystalline tebipenem pivoxil (FIG. 2) ethane sulfonate salt Form A shows a broad endotherm having an onset of 70.8° C. with two minima, the first at 90.7° C. and the second at approximately 108° C. with an enthalpy of fusion of 116 J/g for the first minima and 19 J/g for the second. Degradation occurs above 150° C. for this form.

TGA (also shown in FIG. 2) showed gradual degradation from room temperature to 110° C. with a 2.9% weight loss. No other thermal events were recorded until the onset of degradation beginning at about 150° C.

$^1$H NMR (400 MHz, DMSO-d$_6$) δ ppm 1.05 (t, J=7.45 Hz, 3H) 1.07-1.16 (m, 15H) 2.35 (q, J=7.37 Hz, 2H) 3.07 (s, 1H) 3.28 (dd, J=6.13, 2.72 Hz, 1H) 3.34 (s, 17H) 3.60-3.68 (m, 2H) 3.93 (br t, J=7.52 Hz, 3H) 4.12-4.17 (m, 1H) 4.19 (br d, J=9.47 Hz, 2H) 4.21-4.24 (m, 1H) 4.40-4.49 (m, 1H) 4.68-4.77 (m, 2H) 5.11 (br d, J=4.80 Hz, 1H) 5.75 (d, J=5.81 Hz, 1H) 5.88 (d, J=5.94 Hz, 1H) 10.11 (br s, 1H). $^1$H NMR was consistent with pure tebipenem pivoxil. 1.0 eq. of the esylate counterion was observed.

Example 2. Crystalline Tebipenem Pivoxil Ketoglutarate Salt (IPTG) Form A

Tebipenem pivoxil (35 mg) was dissolved in MeCN (270 μL). The acid stock solution (1 M malic acid in THF) was then added to 1 mol eq. and stirred at 25° C., 500 rpm using a magnetic stir bar in a Polar Bear device for 20 minutes. The sample was then cooled to 5° C. over 2 hours (0.25° C./min) and maintained at 5° C. for ~2 hours. No precipitation was observed so the sample was cooled to −15° C. at 0.5° C./min and stored at −20° C. for 2 days. The solution was transferred to a 20 mL scintillation vial and antisolvent (tert-methyl butyl ether, TBME) was added slowly whilst stirring at 20° C., 500 rpm at a ratio of 10:1 antisolvent: solvent (v/v). A precipitate formed after stirring for 24 hours, which was filtered using a fritted filter and air-dried on a filter block at ambient for 15 minutes.

The XRPD spectra for crystalline tebipenem pivoxil ketoglutarate salt Form A is shown in FIG. 3. The XRPD diffractogram for this crystalline form exhibited the characteristic peaks listed in Table 4. The sample of tebipenem pivoxil ketoglutarate salt crystalline Form A was determined to be 94.5% pure by HPLC, Method A.

An attempt was made to repeat the XRPD and HPLC analysis after one week of storage at 40° C., 75% relative humidity. Post storage XRPD spectra could not be obtained as the sample deliquesced.

TABLE 4

Characteristic angles (2θ) of Tebipenem Pivoxil Ketoglutarate Salt Form A

| Characteristic angle (°) | Relative intensity (%) |
| --- | --- |
| 5.4 | 21.1 |
| 8.6 | 42.6 |
| 9.8 | 18.6 |
| 10.4 | 11 |
| 10.7 | 13.7 |
| 12.7 | 36.5 |
| 13.2 | 27 |
| 13.5 | 51.7 |
| 14.0 | 30.1 |
| 16.2 | 42.8 |
| 17.0 | 80.6 |
| 17.2 | 100.0 |
| 17.7 | 82.9 |
| 18.0 | 16.5 |
| 18.7 | 59.1 |
| 18.9 | 28.3 |
| 19.4 | 25.1 |
| 19.6 | 58.3 |
| 20.0 | 77.8 |
| 20.7 | 37 |
| 21.1 | 64.2 |
| 21.6 | 39.7 |
| 21.8 | 29 |
| 22.7 | 28.5 |
| 23.0 | 37 |
| 23.6 | 56.9 |
| 24.6 | 18.6 |
| 26.7 | 35.4 |
| 27.1 | 26.3 |
| 27.4 | 22.6 |
| 28.3 | 17.8 |
| 28.7 | 25.2 |
| 29.6 | 18 |

The DSC profile for crystalline tebipenem pivoxil (FIG. 4) ketoglutarate salt Form A shows a broad endotherm having an onset of 36.6° C. with and a minima at 57.0° C. with an enthalpy of fusion of 10 J/g, a second endotherm having an onset of 106.5° C. and a minima 117.0° C., with a heat of melting of 12 J/g, and an exotherm with a peak at 126.4° C. during degradation.

TGA (also shown in FIG. 4) shows 0.7% weight loss from room temperature to 75° C.

$^1$H NMR (400 MHz, DMSO-$d_6$) δ ppm 1.06-1.17 (m, 16H) 2.45 (t, J=6.63 Hz, 2H) 2.85 (br t, J=6.25 Hz, 2H) 2.97-2.97 (m, 1H) 3.24-3.27 (m, 2H) 3.28-3.40 (m, 21H) 3.43 (s, 4H) 3.81-3.92 (m, 4H) 3.93-4.00 (m, 1H) 4.18 (dd, J=9.47, 2.65 Hz, 1H) 4.31-4.38 (m, 1H) 4.44 (d, J=8.46 Hz, 2H) 4.98-4.98 (m, 1H) 5.10 (br s, 1H) 5.74 (d, J=5.81 Hz, 1H) 5.89 (d, J=5.94 Hz, 1H). $^1$H NMR was consistent with pure tebipenem pivoxil. 1.0 eq. of the ketoglutarate counterion was observed.

Example 3. Crystalline Tebipenem Pivoxil Maleate (MAE) Salt Form A

Tebipenem pivoxil (J07492, 35 mg) was dissolved in MeCN (270 μL), then the acid stock solution (1 M maleic acid in THF) was added to 1 mol eq. and stirred at 25° C., 500 rpm using a magnetic stir bar in a Polar Bear device for 20 minutes. The sample was then cooled to 0° C. over a 2 hour period (0.2° C./min) and maintained at 0° C. for approximately 1-2 hours. The solution was transferred to a 20 mL scintillation vial and antisolvent (tert-methyl butyl ester, TBME) was added slowly while stirring at 20° C., 500 rpm to a ratio of 4:1 antisolvent:solvent (v/v). A precipitate formed after stirring for 24 hours, which was filtered using a fritted filter and air-dried on a filter block at ambient for 15 minutes.

The XRPD spectra for crystalline tebipenem pivoxil maleate salt Form A is shown in FIG. 5. The XRPD diffractogram for this crystalline form exhibited the characteristic peaks listed in Table 5. The sample of tebipenem pivoxil maleate salt crystalline Form A was determined to be 99.3% pure by HPLC, Method A.

XRPD and HPLC analyses were repeated after one week of storage at 40° C., 75% relative humidity. The XRPD diffractogram showed that Form A had converted to Form B. The tebipenem pivoxil maleate salt Form B, post storage, was 78.6% pure by HPLC, Method A.

TABLE 5

Characteristic Angles (2θ) of Tebipenem Pivoxil Maleate Salt Form A

| Characteristic angle (°) | Relative intensity (%) |
|---|---|
| 8.0 | 36.9 |
| 8.6 | 22.7 |
| 10.8 | 13.0 |
| 11.2 | 16.7 |
| 11.9 | 16.4 |
| 12.2 | 20.1 |
| 12.6 | 58.2 |
| 15.0 | 43.6 |
| 15.4 | 44.6 |
| 15.7 | 42.0 |
| 16.9 | 36.5 |
| 18.2 | 37.4 |
| 18.7 | 100 |
| 19.4 | 43.9 |
| 19.9 | 66.0 |
| 20.4 | 44.0 |
| 21.2 | 33.9 |
| 22.5 | 24.4 |
| 23.1 | 20.6 |
| 24.2 | 24.4 |
| 24.8 | 51.0 |
| 25.7 | 37.8 |
| 26.5 | 41.4 |
| 27.5 | 17.8 |
| 28.3 | 21.0 |

The DSC profile for crystalline tebipenem pivoxil (FIG. 6) maleate salt Form A shows a broad melting endotherm having an onset of 50.6° C. with a minima at 74.3° C. with an enthalpy of fusion of 53 J/g, a second endotherm having an onset of 103.0° C. and a minima 110.1° C., with an enthalpy of fusion of 32 J/g, and an exotherm with a peak at 139.5° C. prior to degradation.

TGA (also shown in FIG. 6) shows 3.6% weight loss from room temperature to 100° C.

$^1$H NMR (400 MHz, DMSO-$d_6$) δ ppm 1.06-1.18 (m, 16H) 2.07 (s, 1H) 3.07 (s, 1H) 3.07-3.08 (m, 1H) 3.12-3.12 (m, 1H) 3.27 (dd, J=6.19, 2.78 Hz, 2H) 3.34 (br dd, J=9.28, 7.26 Hz, 5H) 3.60 (t, J=7.52 Hz, 2H) 3.89-4.01 (m, 3H) 4.07-4.22 (m, 3H) 4.38-4.47 (m, 1H) 4.67 (td, J=8.87, 3.85 Hz, 2H) 5.11 (br d, J=5.05 Hz, 1H) 5.75 (d, J=5.94 Hz, 1H) 5.88 (d, J=5.94 Hz, 1H) 6.05 (s, 2H). $^1$H NMR was consistent with pure tebipenem pivoxil. 0.97 eq. of the maleate counterion was observed.

Example 4. Crystalline Tebipenem Pivoxil Maleate (MAE) Salt Form B

Crystalline tebipenem pivoxil maleate salt Form B was prepared as follows. Tebipenem pivoxil (mg) was dissolved in MeCN (270 μL). The acid stock solution (1 M maleic acid in THF) was then added to 1 mol eq. and stirred at 25° C., 500 rpm using a magnetic stir bar in a Polar Bear device for 20 minutes. The sample was then cooled to 5° C. over a 2 hour period (0.25° C./min) and maintained at 5° C. for approximately 2 hours. No precipitation was observed. The sample was then cooled to −15° C. at 0.5° C./min and stored at −20° C. for 2 days. The solution was transferred to a 20 mL scintillation vial and antisolvent (tert-methyl butyl ether, TBME) was added slowly whilst stirring at 25° C., 500 rpm, at a ratio of 5:1 antisolvent:solvent (v/v). A precipitate formed after stirring for 24 hours. The precipitate was filtered using a fritted filter and air-dried on a filter block at ambient for 15 minutes.

The XRPD diffractogram for this crystalline form exhibited the characteristic peaks listed in Table 6.

The XRPD spectra for crystalline tebipenem pivoxil maleate salt Form B is shown in FIG. 7. The sample of tebipenem pivoxil maleate salt crystalline Form B was determined to be 99.3% pure by HPLC, Method A.

The XRPD and HPLC analysis were repeated after one week of storage at 40° C., 75% relative humidity. The XRPD diffractogram showed characteristic peaks for tebipenem pivoxil maleate crystalline Form B. The tebipenem pivoxil maleate salt Form B, post storage, was 90.2% pure by HPLC, Method A.

TABLE 6

Characteristic angles (2θ) of Tebipenem Pivoxil Maleate Acid Salt Form B

| Characteristic angle (°) | Relative intensity (%) |
|---|---|
| 5.5 | 24 |
| 8.9 | 29.1 |
| 10.1 | 14.7 |
| 10.6 | 10.1 |
| 11.0 | 34.5 |
| 12.8 | 15.7 |
| 13.6 | 25.5 |
| 14.3 | 19.8 |
| 14.9 | 6.8 |
| 16.7 | 28.4 |
| 17.0 | 88.2 |
| 17.2 | 29.6 |
| 17.9 | 7.4 |
| 18.6 | 41.8 |
| 19.0 | 29.1 |
| 19.4 | 14.5 |
| 20.2 | 32.7 |
| 20.5 | 16.2 |
| 20.8 | 53.9 |
| 21.4 | 100 |
| 21.9 | 25.8 |
| 22.2 | 26.3 |
| 23.1 | 14.5 |
| 24.0 | 43 |
| 24.5 | 11.3 |
| 25.1 | 11.8 |
| 25.5 | 16.3 |
| 26.2 | 16.2 |
| 27.5 | 17.8 |
| 28.1 | 19.1 |
| 28.9 | 16.8 |
| 29.6 | 10.6 |

The DSC profile for crystalline tebipenem pivoxil (FIG. 8) maleate salt Form B shows a broad endotherm having an onset of 40.3° C. with a minima at 65.3° C. and an enthalpy of fusion of 77 J/g, a second endotherm having an onset of 114.7° C. and a minima of 119.6° C., with an enthalpy of fusion of 25 J/g, and an exotherm with a peak at 140.3° C. prior to degradation.

TGA (also shown in FIG. 8) shows 4.6% weight loss from room temperature to 100° C.

$^1$H NMR (400 MHz, DMSO-$d_6$) δ ppm −0.21-−0.21 (m, 1H) 1.07-1.16 (m, 15H) 3.07 (s, 1H) 3.27 (dd, J=6.19, 2.78 Hz, 2H) 3.29-3.40 (m, 23H) 3.60 (t, J=7.52 Hz, 2H) 3.89-4.02 (m, 3H) 4.06-4.16 (m, 2H) 4.19 (dd, J=9.54, 2.72 Hz, 1H) 4.37-4.48 (m, 1H) 4.61-4.73 (m, 2H) 5.11 (d, J=5.18 Hz, 1H) 5.75 (d, J=5.81 Hz, 1H) 5.89 (d, J=5.94 Hz, 1H) 6.05 (s, 2H). $^1$H NMR was consistent with pure tebipenem pivoxil. Approximately 0.92 eq. of the maleate counterion was observed.

Example 5. Crystalline Tebipenem Pivoxil Malate (MAL) Salt Form A

Tebipenem pivoxil (35 mg) was dissolved in MeCN (270 μL). The acid stock solution (1 M malic acid in THF) was added to 1 mol eq. and stirred at 25° C., 500 rpm using a magnetic stir bar in a Polar Bear device for 20 minutes. The sample was then cooled to 0° C. over a 2 hour period (0.2° C./min) and maintained at 0° C. for about 2 hours. No precipitation was observed so the sample was cooled to −15° C. at 0.5° C./min and stored at −20° C. for 2 days. The solution was transferred to a 20 mL scintillation vial and antisolvent (tert-methyl butyl ether, TBME) was added slowly while stirring at 25° C., 500 rpm at a ratio of 4:1 antisolvent:solvent (v/v). A precipitate formed after stirring for 24 hours, which was filtered using a fritted filter and air-dried on a filter block at ambient for 15 minutes. The XPRD diffractogram for crystals prepared according to this procedure is shown in FIG. 9. The peak listing for this diffractogram is provided in Table 7.

Figure 10:
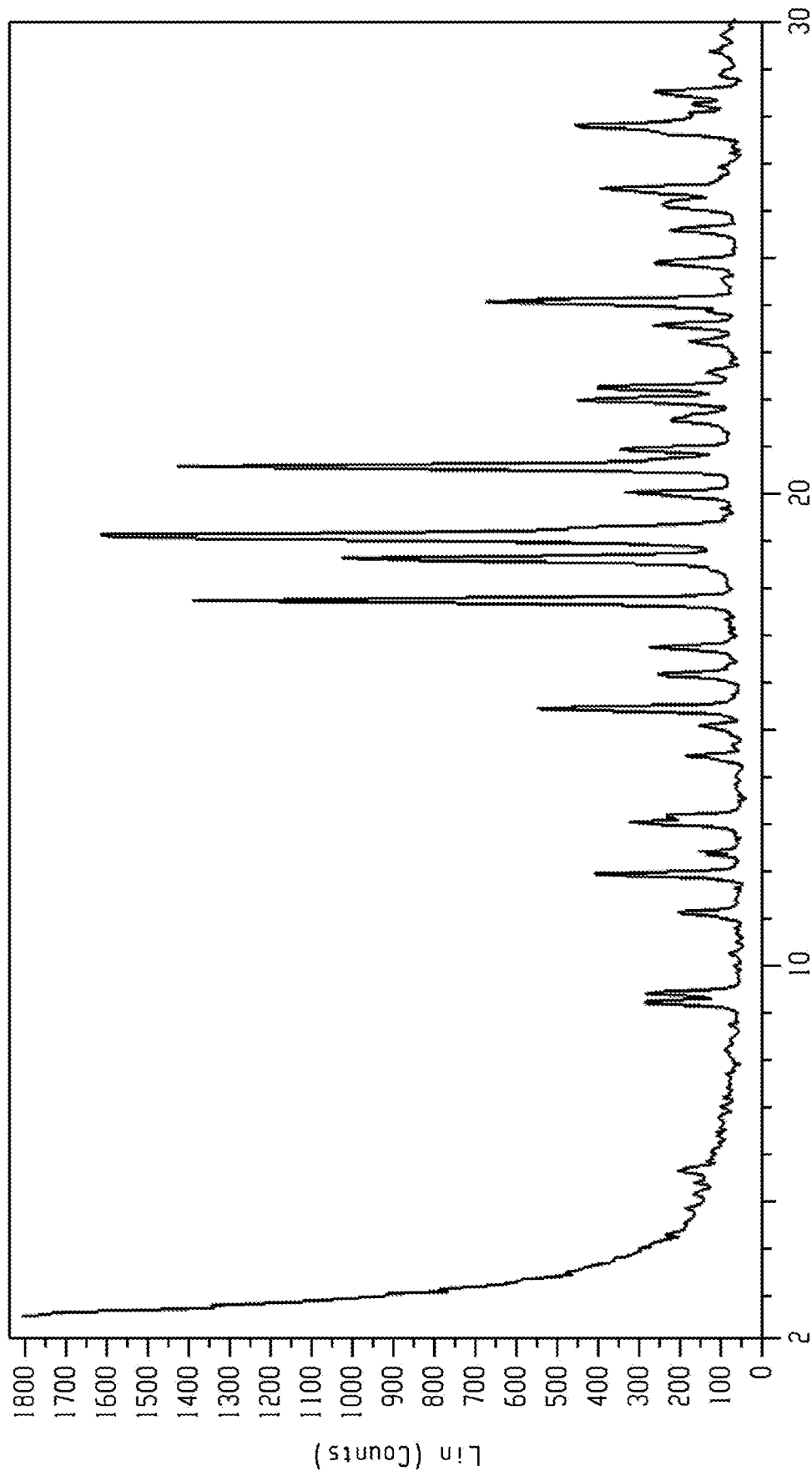
FIG. 10. XRPD diffractogram of crystalline tebipenem pivoxil malate salt Form A prepared by method 2 in which tebipenem pivoxil is dissolved in MeCN.

Crystalline tebipenem pivoxil malate salt was also obtained at equivalent purity using the method in the preceding paragraph but with the following changes. Tebipenem pivoxil was dissolved in EtOH (930 μL). The acid stock solution (1 M malic acid in THF) was added to 1 mol eq. and stirred at 25° C., 500 rpm using a magnetic stir bar in a Polar Bear device for 20 minutes. The sample was then cooled to 5° C. over approximately 2 hours (0.2° C./min) and maintained at 5° C. for about 2 hours. The sample was subsequently cooled to −15° C. at 0.2° C./min and stored at −20° C. for 24 hours. The solution was transferred to a 20 mL scintillation vial and antisolvent (n-hexane) was added slowly whilst stirring at 25° C., 500 rpm until a precipitate formed at a ratio of 3:1 antisolvent:solvent (v/v). The suspension obtained was filtered using a fritted filter and air-dried on a filter block at ambient for 15 minutes. The XRPD for crystals prepared by this method is shown in FIG. 10.

TABLE 7

Characteristic angles (2θ) Tebipenem Pivoxil Malate Salt Form A

| Characteristic angle (°) | Relative intensity (%) |
|---|---|
| 9.1 | 22.9 |
| 9.3 | 18.7 |
| 11.0 | 11.4 |
| 11.8 | 25.4 |
| 12.3 | 12.9 |
| 12.9 | 23.6 |
| 13.1 | 21.4 |
| 14.4 | 11.9 |
| 14.9 | 14.2 |
| 15.3 | 35.1 |
| 16.0 | 20.1 |
| 16.6 | 15.9 |
| 17.6 | 89.3 |
| 18.5 | 56.5 |
| 19.0 | 100 |
| 19.9 | 26.6 |
| 20.5 | 81.6 |
| 20.8 | 28.6 |
| 21.4 | 20.6 |
| 21.9 | 37.1 |
| 22.2 | 33.1 |
| 23.1 | 14.9 |
| 23.4 | 16.2 |
| 23.9 | 36.8 |
| 24.8 | 20.4 |
| 25.5 | 17.2 |
| 26.0 | 20.1 |
| 26.3 | 27.1 |
| 27.7 | 25.9 |
| 28.4 | 24.4 |

The DSC profile for crystalline tebipenem pivoxil (FIG. 11) malate salt Form A shows a melting endotherm having an onset of 32.1° C. with a minima at 51.1° C. and an enthalpy of fusion of 9 J/g, with a second endotherm having an onset of 117.0° C. and a minima 127.6° C., with a heat of melting of 23 J/g, and an exotherm with a peak at 131.6° C. with a heat of 44 J/g.

TGA (also shown in FIG. 11) shows 0.7% weight loss from room temperature to 75° C., and a 0.3% weight loss from 75° C. to 130° C.

$^1$H NMR (400 MHz, DMSO-$d_6$) δ ppm 1.07-1.16 (m, 16H) 2.41 (dd, J=15.66, 7.20 Hz, 1H) 2.59 (dd, J=15.60, 5.75 Hz, 1H) 3.07 (s, 1H) 3.25 (dd, J=6.32, 2.65 Hz, 1H) 3.32 (br dd, J=9.35, 7.33 Hz, 5H) 3.39 (t, J=7.52 Hz, 3H) 3.68-3.68 (m, 1H) 3.76-3.83 (m, 2H) 3.88 (t, J=7.58 Hz, 2H) 3.96 (br s, 1H) 4.15-4.18 (m, 1H) 4.15-4.22 (m, 1H) 4.29-4.44 (m, 3H) 5.04-5.04 (m, 1H) 5.09 (br s, 1H) 5.74 (d, J=5.94 Hz, 1H) 5.89 (d, J=5.94 Hz, 1H). $^1$H NMR was consistent with pure tebipenem pivoxil. Approximately 1.09 eq. of the malate counterion was observed. XRPD was attempted one week post storage at 40° C. and 75% relative humidity. The sample was found to have deliquesced to an orange liquid. No HPLC analysis of the post storage sample was performed.

Example 6. Tebeipenem Pivoxil Methane Sulfonate Salt (MSA) Form B

Tebipenem pivoxil (35 mg) was dissolved in MeCN (270 μL). The acid stock solution (1 M methane sulfonic acid in THF) was then added to 1 mol eq. and stirred at 25° C., 500 rpm using a magnetic stir bar in a Polar Bear device for 20 minutes. The sample was then cooled to 0° C. over 2 hours (0.2° C./min) and maintained at 0° C. for about 2 hours. No precipitation was observed so the sample was cooled to −15° C. at 0.5° C./min and stored at −20° C. for 2 days. The solution was transferred to a 20 mL scintillation vial and antisolvent (tert-methyl butyl ether, TBME) was added slowly whilst stirring at 25° C., 500 rpm until a precipitate formed at a ratio of 3:1 antisolvent:solvent (v/v). The suspension obtained was filtered using a fritted filter and air-dried on a filter block at ambient for 15 minutes. Crystalline material obtained by this procedure was determined to be 99.5% pure by HPLC, Method A. The XRPD diffractogram for this form is shown in FIG. 12. Characteristic peaks are listed in Table 8.

The MSA salt was also obtained in the same crystalline form at equivalent purity using the method in the preceding paragraph but with the following changes. Tebipenem pivoxil was dissolved in EtOH (930 μL). The acid stock solution (1 M methane sulfonic acid in THF) was added to 1 mol eq. and stirred at 25° C., 500 rpm using a magnetic stir bar in a Polar Bear device for 20 minutes. The sample was then cooled to 5° C. over approximately 2 hours (0.2° C./min) and maintained at 5° C. for about 2 hours. The sample was subsequently cooled to −15° C. at 0.2° C./min and stored at −20° C. for 24 hours. The solution was transferred to a 20 mL scintillation vial and antisolvent (n-hexane) was added slowly whilst stirring at 25° C., 500 rpm until a precipitate formed at a ratio of 3:1 antisolvent:solvent (v/v). The suspension obtained was filtered using a fritted filter and air-dried on a filter block at ambient for 15 minutes.

TABLE 8

Characteristic angles (2θ) of Tebipenem Pivoxil Methane Sulfonate Salt Form B

| Characteristic angle (°) | Relative intensity (%) |
|---|---|
| 9.1 | 10.8 |
| 9.6 | 31.5 |
| 10.9 | 33.8 |
| 12.6 | 24.6 |
| 13.9 | 27 |
| 14.6 | 6.2 |
| 15.4 | 54.5 |
| 17.2 | 90.1 |
| 17.5 | 12.4 |
| 18.2 | 17.2 |
| 18.4 | 41.7 |
| 18.7 | 30.7 |
| 19.4 | 100 |
| 19.6 | 66.5 |
| 19.8 | 33.1 |
| 20.4 | 67.1 |
| 20.6 | 20.5 |
| 21.5 | 46.9 |
| 21.9 | 17.1 |
| 22.2 | 99.8 |
| 22.9 | 18 |
| 23.6 | 23.4 |
| 24.5 | 12.2 |
| 25.3 | 11.1 |
| 25.6 | 13.8 |
| 26.4 | 16.3 |
| 26.9 | 22.3 |
| 27.1 | 15.8 |
| 27.5 | 9 |
| 27.8 | 13.1 |
| 28.0 | 24.1 |
| 28.6 | 32.1 |
| 29.4 | 25.8 |
| 29.8 | 13.8 |

The DSC profile for crystalline tebipenem pivoxil (FIG. 13) methane sulfonate salt Form B shows a melting endotherm having an onset of 57.8 ° C. with a minima at 88.5° C. and a heat of melting of 105 J/g, a second endotherm having an onset of 175.2° C. and a minima 177.0° C., with a heat of melting of 48 J/g prior to degradation.

TGA (also shown in FIG. 13) shows 2.9% weight loss from room temperature to 100° C. No other thermal events were note until the onset of degradation.

$^1$H NMR (400 MHz, DMSO-d$_6$) δ ppm 1.07-1.18 (m, 16H) 2.07 (s, 1H) 2.30 (s, 2H) 2.27-2.31 (m, 1H) 3.07 (s, 1H) 3.28 (dd, J=6.13, 2.59 Hz, 1H) 3.30-3.46 (m, 6H) 3.61-3.69 (m, 2H) 3.90-4.01 (m, 3H) 4.13-4.28 (m, 3H) 4.40-4.50 (m, 1H) 4.70-4.79 (m, 2H) 5.11 (br s, 1H) 5.75 (d, J=5.94 Hz, 1H) 5.88 (d, J=5.94 Hz, 1H) 10.12 (br s, 1H). $^1$H NMR (not shown) was consistent with pure tebipenem pivoxil. Approximately 1.06 eq. of the methane sulfonate counterion was observed when the analysis was adjusted for solvent by TGA. XRPD and HPLC were performed one week post storage at 40° C. and 75% relative humidity. The XRPD diffractogram was consistent with pure tebipenem pivoxil methane sulfonate crystalline Form B. The sample was 99.0% pure by HPLC, Method A.

Example 7. Large Scale Preparation of Tebipenem Pivoxil HBR Methane Sulfonate Salt (MSA) Form B Tebipenem Pivoxil (125 mg) was placed into eight separate 20 ml scintillation vials and dissolved in MeCN (7.5 vol, 940 μl) while stirring at 25° C., 500 rpm using a magnetic stirrer bar on a Polar Bear device. The sample was treated with 1 mol eq. of the acid stock (1M methane sulphonic acid stock in THF) and cooled to 5° C. No precipitation was observed at 5° C., and the temperature was raised to 20° C. Antisolvent (TBME) was then added, whilst stirring at 20° C. to a 2:1 ratio (antisolvent:solvent (v/v) ratio) for 1 hour. The resulting suspensions were filtered through a fritted filter, dried under suction for 15 minutes and each sample analysed by XRPD. Samples exhibiting the XRPD pattern of mesylate Form B were pooled together for characterisation. Characteristic peaks of the XRPD diffractogram are listed in Table 10.

TABLE 9

Solid-state characterisation of scaled-up Tebipenem Pivoxil MSA Form B

| | |
|---|---|
| Obtained by | Antisolvent addition at 20° C. (TBME:MeCN, 2:0 |
| XRPD | Crystalline Mesylate Form B |
| $^1$H NMR | $^1$H NMR consistent with supplied. ~1.03 eq Mesylate, ~0.03 eq ACN |
| Anion IC (eq.) | 0.97 (not adjusted for solvent) |
| HPLC, Method B | 99.4% |
| GVS (Gravimetric Vapor Sorption) and XRPD analysis post GVS | Sample is hygroscopic. 6.2% uptake from 0 to 90% RH. Isotherm shows steps from 0 to 10% RH (3.0 % wt.) and 80 to 90% RH (1.4% wt.). No change by XRPD post GVS. |
| DSC | Broad endo at 68.8° C. (onset), 88 J/g. Endo at 140.7° C. (onset), 16 J/g, prior to degradation ~160° C. |
| TGA | 3.5% wt, loss from RT to 120° C. |
| KF | 3.3% water, ~1 eq. water |
| PLM | Crystals and particles, 10-150 μm diameter |
| XRPD analysis post storage at 40° C./75% RH and 25° C./ 97% RH for 1-4 weeks | Unchanged by XRPD after 1 week, and was a powder post-25/97 but a gum post-40/75. HPLC after 1 week: 40/75: 95.5%, 25/97: 96.5%. Sample deliquesced within 2 weeks |
| VT-XRPD on C2 | Some changes upon heating up to 100° C. Sample degrades ~160° C. |

TABLE 10

Peak listing for XRPD diffractogram of MSA salt Form B

| Angle (2-Theta °) | Intensity (%) |
|---|---|
| 9.1 | 6.7 |
| 9.7 | 17.9 |
| 10.9 | 19.6 |
| 12.6 | 16.7 |
| 13.9 | 15.9 |
| 15.4 | 35 |
| 17.2 | 52.1 |
| 17.5 | 8.8 |
| 18.2 | 14 |
| 18.4 | 19.9 |
| 18.7 | 18.1 |
| 19.4 | 100 |
| 19.6 | 40.2 |
| 19.8 | 20.9 |
| 20.4 | 36.2 |
| 21.5 | 25.3 |
| 21.9 | 8.4 |
| 22.2 | 45.1 |
| 22.9 | 10.1 |
| 23.6 | 11.6 |
| 24.5 | 6.2 |
| 25.3 | 6.3 |
| 25.5 | 8.2 |
| 26.5 | 8.3 |
| 26.8 | 12.4 |
| 27.5 | 5.5 |
| 28 | 10.5 |
| 28.6 | 16.4 |
| 29.3 | 11.3 |

Example 8. Tebeipenem Pivoxil Methane Sulfonate Salt (MSA) Form C

Tebipenem Pivoxil (1 g) was dissolved in MeCN (8 vol, 8 ml) and 1 mol eq. of the acid stock (1 M methane sulphonic acid in THF, 2 ml) added whilst stirring at 25° C., 500 rpm. Antisolvent (TBME) was then added to a 2:1 ratio (antisolvent:solvent (v/v) ratio) and a precipitate began to form. Further antisolvent was added to a ratio of 5:1 and the precipitate was then cooled to 0° C. at 0.2° C./min. On reaching 0° C. the sample was removed and rapidly cooled in a dry ice/acetone bath to complete precipitation. The solid was filtered under vacuum into a Buchner funnel and dried under vacuum at RT for 16 hours.

Figure 25:
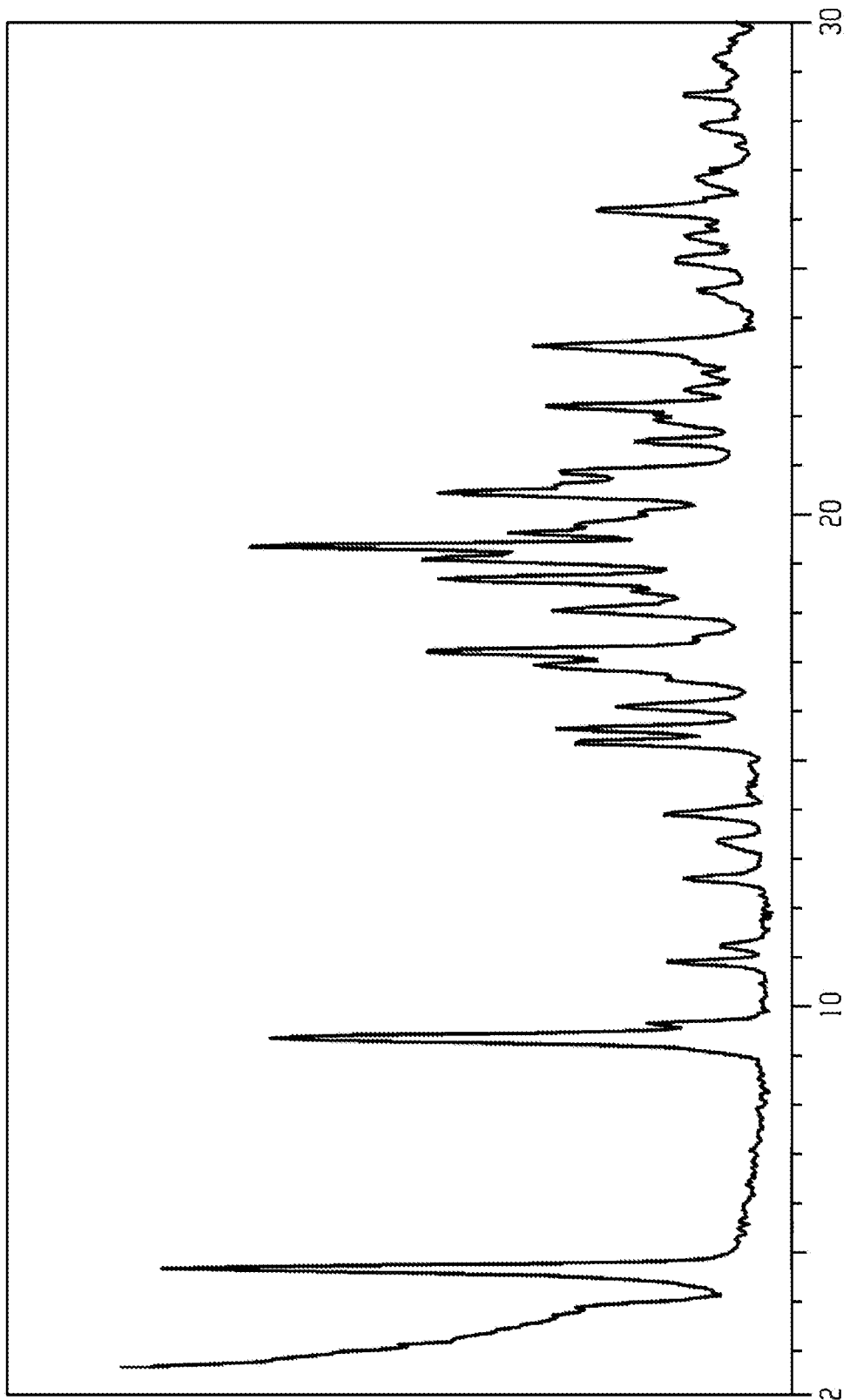
FIG. 25. XRPD diffractogram of crystalline tebipenem pivoxil methane sulfonate salt Form B+C.
Figure 26:
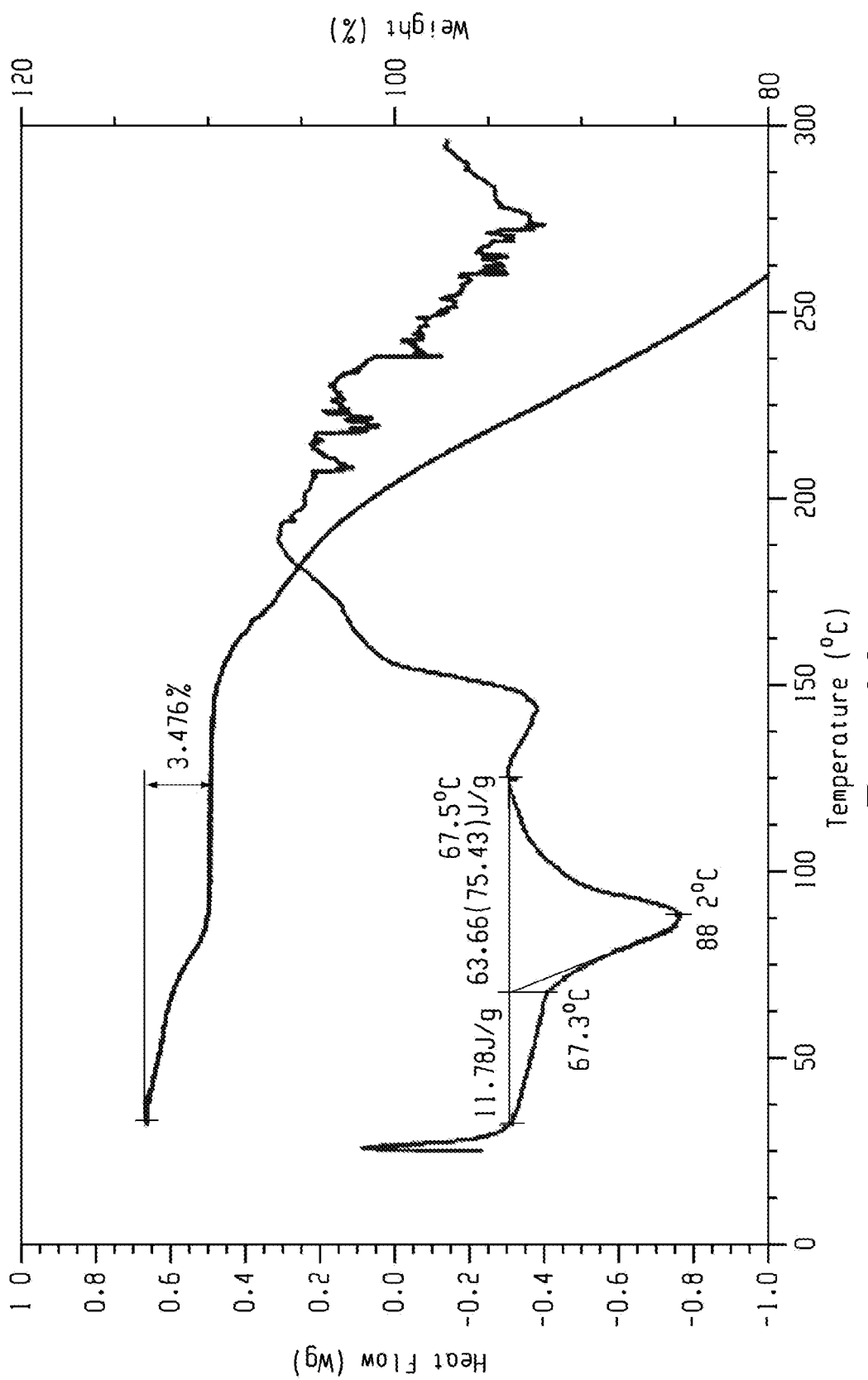
FIG. 26. DSC and TGA profiles of crystalline tebipenem pivoxil methane sulfonate salt Form B+C.

XRPD analysis of the resulting solid showed the material was a mixture of mesylate Form C and Form B. A sample of pure Form C could not be generated, therefore this sample was further characterised as detailed below. The XRPD diffractogram for Form C+Form B is provided at FIG. 25 and the DSC and TGA plots are provided at FIG. 26.

TABLE 11

Solid-state characterisation of Tebipenem Pivoxil Mesylate Form C + Form B

| | |
|---|---|
| Obtained by | Antisolvent addition at 25° C. (TBME:MeCN, 2:1) |
| XRPD | Crystalline, Mesylate Form C + Form B |
| $^1$H NMR | $^1$H NMR consistent with supplied. ~1.08 eq Mesylate. Trace residual MeCN and TBME seen. |
| Anion IC (eq.) | 1.01 (not adjusted for solvent) |
| HPLC, Method B | 99.1% |
| GVS and XRPD analysis post GVS | Sample is hygroscopic. 10.0% uptake from 0 to 90% RH, with two steps at 0-10% & 80-90% RH Reversible uptake and loss. XRPD post-GVS showed conversion to mesylate Form B. |
| DSC | Broad endotherm from 30 to 120° C. Peak at 88.2° C., 75 J/g. Sample degrades ~140° C. |
| TGA | 3.5% wt. loss from RT to 120° C. |
| KF | NIP |
| PLM | NIP |
| XRPD analysis post storage at 40° C./75% RH and 25° C./97% RH for 1-4 weeks | Sample deliquesced to an orange liquid within 1 week. No XRPD analyses collected |
| VT-XRPD on C2 | No changes upon heating. Sample melt/degrades ~140° C. |

Example 9. Tebeipenem Pivoxil Methane Sulfonate Salt (MSA) Form D

Tebipenem Pivoxil (30 mg) was dissolved in t-BuOH (30 vol., 940 μl) while stirring at 50° C., 500 rpm using a magnetic stirrer bar on a Polar Bear device. The sample was treated with 1 mol eq. of acid stock (1 M HBr aq. in THF, 60 μl), then frozen in a dry ice/acetone bath and lyophilised for 16 hours. To the resulting white solid was added THF (30 vol, 900 μl) while stirring at 25° C., 500 rpm. The suspension was heated to 50° C. and then cooled to 5° C. at 0.2° C./min and held at 5° C. for 12 hours. An aliquot of the suspension was filtered on a Millipore 96-well filter block, dried under suction for 10 minutes and analysed by XRPD. The suspension was stirred at 25° C. for 4 hours and then filtered on a Millipore 96-well filter block, dried under vacuum for 10 minutes and analysed by XRPD.

Figure 27:
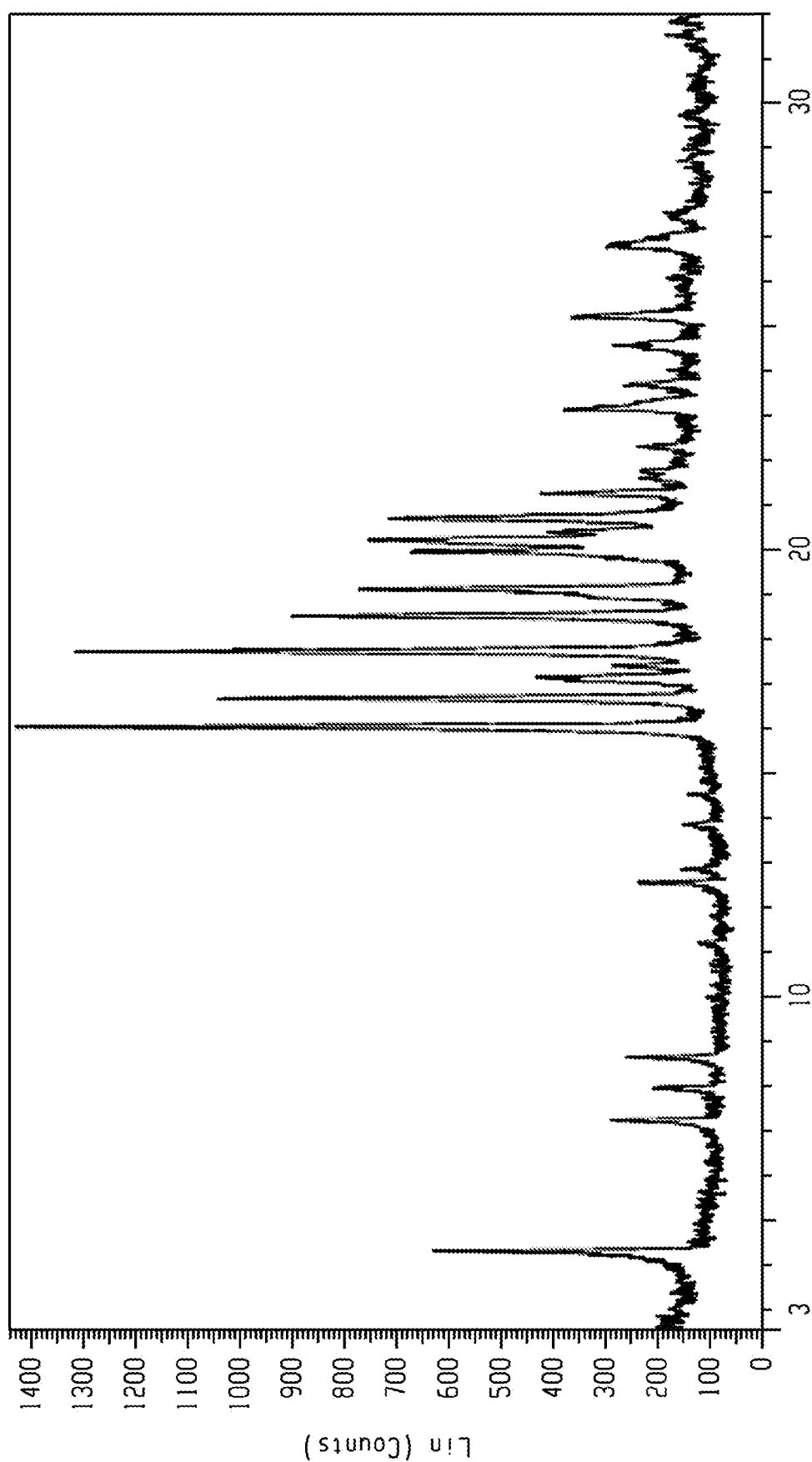
FIG. 27. XRPD diffractogram of crystalline tebipenem pivoxil methane sulfonate salt Form D.

XRPD analysis of an aliquot of solid post-cooling showed the material was mesylate Form D. After maturing at 25° C. for 4 hours, XRPD analysis showed a mixture of mesylate Form D and Form B. A sample of pure Form D could not be generated by scale-up experiments, therefore this sample was further characterised as detailed in Table 12. The XRPD for this crystalline form is shown in FIG. 27.

TABLE 12

Solid-state characterisation of Tebipenem Pivoxil MSA Form D identified from screens

| XRPD post-cooling, pre-maturation | XRPD post-maturation | DSC | TGA | $^1$H NMR | HPLC | Storage at 40° C./75% RH and 25° C./97% RH |
|---|---|---|---|---|---|---|
| MSA Form D | MSA Form D + Form B | Broad endo from 30 to 100° C. (onset), 95.4 J/g, sharp endo at 173.2° C. (onset) 41 J/g. | 3.8% wt. loss from RT to 100° C. | Consistent with structure, 0.98 eq. MSA, 0.03 eq. THF | 99.6% | Sample converted to Form B after 1 week at 40° C./75% RH. Purity: 99.4% after 1 week at 40° C./75% RH. |

$^1$H NMR (400 MHz, DMSO-d$_6$) δ ppm 1.05-1.18 (m, 16H) 1.76 (br t, J=2.78 Hz, 1H) 2.29 (d, J=1.01 Hz, 3H) 2.48-2.52 (m, 1H) 3.28 (dd, J=6.13, 2.34 Hz, 1H) 3.63 (t, J=7.45 Hz, 2H) 3.89-4.02 (m, 3H) 4.10-4.26 (m, 3H) 4.44 (br s, 1H) 4.66-4.78 (m, 2H) 5.11 (br s, 1H) 5.75 (d, J=5.94 Hz, 1H) 5.88 (d, J=5.94 Hz, 1H) 10.10 (br s, 1H). $^1$H NMR was consistent with pure tebipenem pivoxil.

Figure 28:
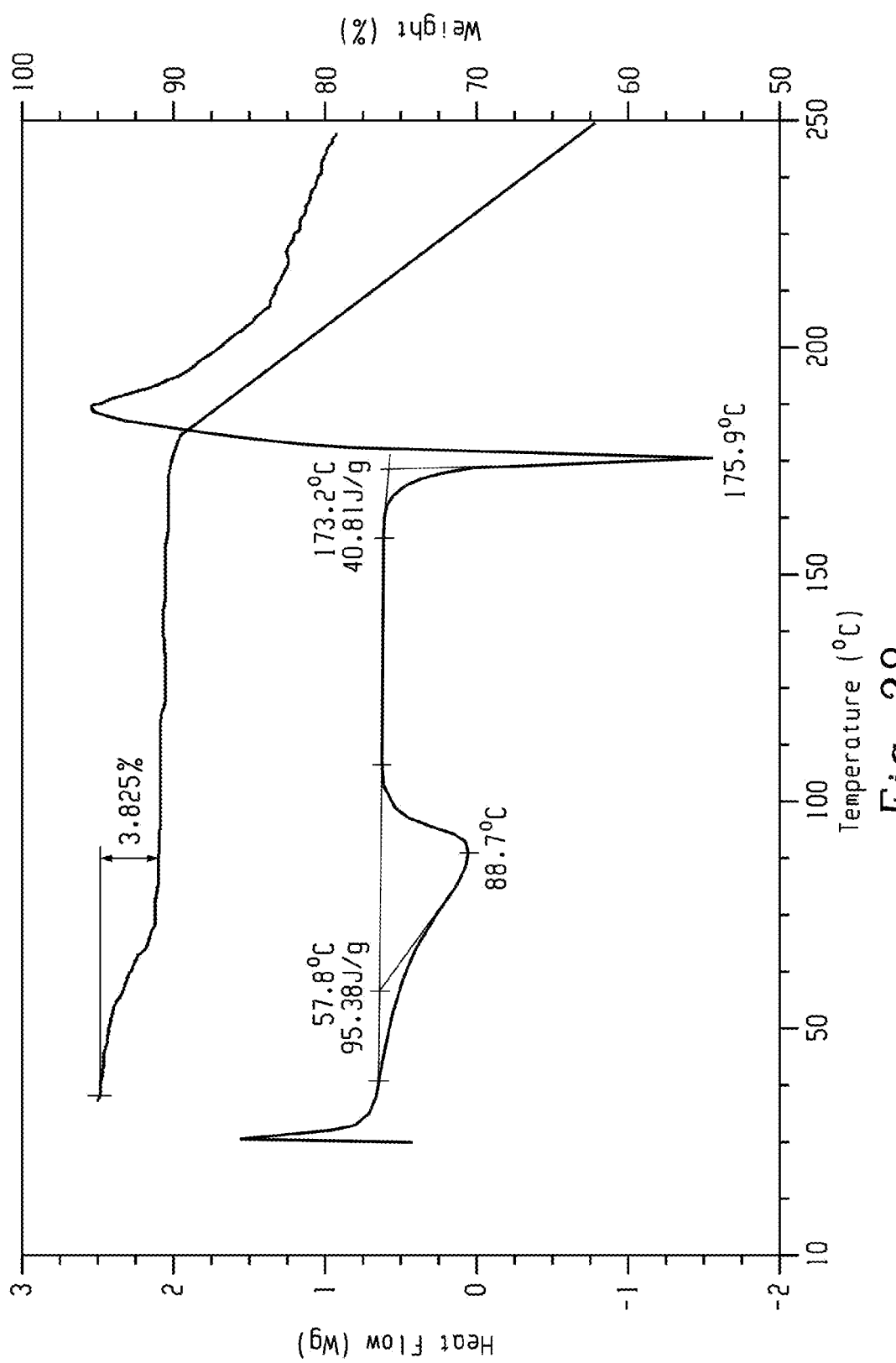
FIG. 28. DSC and TGA profiles of crystalline tebipenem pivoxil methane sulfonate salt Form D+Form B.

Characteristic peaks of the XRPD diffractogram are listed in Table 13 and the XRPD spectra is shown in FIG. 27. The DSC and TGA profiles for Form B+D are shown in FIG. 28.

TABLE 13

Peak listing for XRPD diffractogram of MSA Form D

| Angle (2-Theta °) | Intensity (%) |
|---|---|
| 4.3 | 44.4 |
| 7.2 | 21 |
| 8 | 15.6 |
| 8.7 | 19 |
| 11.2 | 9.8 |
| 12.6 | 17.6 |
| 12.9 | 11.8 |
| 13.8 | 11.6 |
| 14.5 | 10.7 |
| 16.1 | 100 |
| 16.7 | 73.1 |
| 17.2 | 31.1 |
| 17.5 | 20.8 |
| 17.8 | 92.3 |
| 18.5 | 64 |
| 19.1 | 54.3 |
| 20 | 48 |
| 20.2 | 54 |
| 20.4 | 29.8 |
| 20.7 | 51.1 |
| 21.3 | 30.3 |
| 21.6 | 17.2 |
| 21.8 | 17.4 |
| 22.3 | 18.2 |
| 23.2 | 27.8 |
| 23.7 | 19.5 |
| 24.6 | 21.1 |
| 25.2 | 26.9 |
| 26.8 | 22 |
| 27.5 | 13.5 |

Example 10. Crystalline Tebipenem Pivoxil Hydrobromide (HBR) Salt Form B

Tebipenem pivoxil (35 mg) was dissolved in MeCN (270 μL). The counterion (1 M HBr stock in THF) was added to 1 mol eq. and stirred at 25° C., 500 rpm using a magnetic stir bar in a Polar Bear device for 20 minutes. The sample was then cooled to 0° C. over 2 hours (0.2° C./min) and maintained at 0° C. for ~2 hours. The suspension obtained was filtered using a fritted filter and air-dried on a filter block at ambient for 15 minutes. This material was 99.4% pure by HPLC, Method A. The XRPD diffractogram for tebipenem pivoxil HBr crystalline Form B prepared by this method is shown in FIG. 14 and the peak listing is provided in Table 14.

HBr salt was also obtained at equivalent purity using the method in the preceding paragraph but with the following changes. Tebipenem pivoxil was dissolved in EtOH (930 μL). The counterion (1 M HBr stock in THF) was added to 1 mol eq. and stirred at 25° C., 500 rpm using a magnetic stirrer bar in a Polar Bear device for 20 minutes. The sample was then cooled to 5° C. over 2 hours (0.2° C./min) and maintained at 5° C. for about 2 hours.

TABLE 14

Characteristic angles (2θ) of Tebipenem Pivoxil HBr Salt Form B

| Characteristic angle (°) | Relative intensity (%) |
|---|---|
| 9.3 | 50.6 |
| 9.5 | 10 |
| 10.7 | 19.5 |
| 12.6 | 7.2 |
| 13.0 | 17.9 |
| 14.0 | 10.1 |
| 15.2 | 6 |
| 15.7 | 6.2 |
| 17.6 | 100 |
| 18.7 | 17.5 |
| 19.1 | 9.9 |
| 20.0 | 79.4 |
| 20.4 | 13.8 |
| 20.8 | 70.3 |
| 21.1 | 14.4 |
| 21.9 | 10.3 |
| 22.6 | 11.8 |
| 23.5 | 27.2 |
| 23.7 | 11.4 |
| 24.9 | 11.6 |
| 25.3 | 11.5 |
| 25.5 | 17.4 |
| 25.8 | 11.7 |
| 26.1 | 18.4 |
| 26.5 | 10.7 |
| 26.8 | 19.9 |
| 27.3 | 17.1 |
| 27.6 | 16 |
| 28.4 | 19 |
| 28.8 | 13.1 |

TABLE 14-continued

Characteristic angles (2θ) of Tebipenem Pivoxil HBr Salt Form B

| Characteristic angle (°) | Relative intensity (%) |
|---|---|
| 29.4 | 12.1 |
| 29.7 | 15.2 |
| 29.9 | 8.6 |

The DSC profile for crystalline tebipenem pivoxil (FIG. 15) hydrogen bromide salt Form B shows a broad melting endotherm having an onset of 32.9° C. with a minima at 66.3° C. and a heat of melting of 34.1 J/g, and an exotherm having an onset of 186.8° C., with a maxima of 190.8 prior to degradation.

TGA (also shown in FIG. 15) shows 1.9% weight loss from room temperature to 100° C. No other thermal events were noted until the onset of degradation.

$^1$H NMR (400 MHz, DMSO-$d_6$) δ ppm 1.06-1.18 (m, 15H) 3.28 (dd, J=6.19, 2.65 Hz, 1H) 3.30-3.40 (m, 5H) 3.61-3.69 (m, 2H) 3.90-4.01 (m, 3H) 4.13-4.27 (m, 3H) 4.41-4.50 (m, 1H) 4.69-4.79 (m, 2H) 5.00-5.01 (m, 1H) 5.11 (br s, 1H) 5.75 (d, J=5.94 Hz, 1H) 5.88 (d, J=5.94 Hz, 1H) 10.11 (s, 1H). $^1$H NMR was consistent with pure tebipenem pivoxil. Approximately 1.04 eq. of the hydrogen bromide counterion was observed when the analysis was adjusted for solvent by TGA. XRPD and HPLC were performed one week post storage at 40° C. and 75% relative humidity. The XRPD diffractogram was consistent with pure tebipenem pivoxil HBr crystalline Form B. The sample was 99.2% pure by HPLC.

Example 11. Crystalline Tebipenem Pivoxil Hydrobromide (HBR) Salt Form C

Tebipenem Pivoxil (30 mg) was dissolved in t-BuOH (940 μl) while stirring at 50° C., 500 rpm using a magnetic stirrer bar in a Polar Bear device. The sample was treated with 1 mol eq. of acid stock (1 M HBr aq. in THF, 60 μl), then frozen in a dry ice/acetone bath and lyophilised for 16 hours. To the resulting white solid was added 1,2-dimethoxyethane (10 vol, 300 μl) whilst stirring at 50° C. Additional solvent was added to a final volume of 30 vol. (900 μl) to allow effective stirring of the suspension. The suspension was cooled to 5° C. at 0.2 ° C./min, and maintained at 25° C. for 72 hours. The suspension obtained was filtered on a Millipore 96-well filter block and dried under suction for 15 minutes.

TABLE 15

Solid-state characterisation of Tebipenem Pivoxil HBr Form C

| XRPD | Crystalline, Form C |
|---|---|
| $^1$H NMR | Consistent with HBr salt Form A |
| | No residual solvent. |
| HPLC (%, AUC) | 99.8% |
| DSC | No significant thermal events until exotherm at onset of degradation, at 179.5° C. (onset). |
| TGA | 0.5% wt. loss from RT to 140° C. and an onset of degradation of 181.8° C. |
| XRPD analysis post storage at 40° C./75% RH for | Unchanged by XRPD (Form C). Peak intensity decreased, suggesting reduced crystallinity. |
| 1 week | HPLC purity post-storage = 99.9% |
| Anion IC | 0.92 eq. (not adjusted for solvent) |
| GVS and XRPD post-GVS | N/P |

Characteristic peaks of the XRPD diffractogram are listed in Table 16.

TABLE 16

Peak listing for XRPD diffractogram of Tebipenem Pivoxil HBr Form C

| Angle (2-Theta °) | Intensity % |
|---|---|
| 4.4 | 72.6 |
| 8.7 | 15.6 |
| 9.3 | 17.1 |
| 12 | 18.4 |
| 13.1 | 21.4 |
| 13.6 | 11.3 |
| 14.2 | 5.8 |
| 15.5 | 10.4 |
| 16.3 | 29.7 |
| 16.5 | 20.8 |
| 17.1 | 18.1 |
| 17.3 | 21.4 |
| 17.6 | 19.3 |
| 18.5 | 9.6 |
| 19.3 | 14.4 |
| 19.7 | 18.7 |
| 20.8 | 26.1 |
| 21 | 21.4 |
| 21.3 | 20.7 |
| 21.7 | 100 |
| 22.2 | 21.3 |
| 22.6 | 22.2 |
| 22.8 | 11.6 |
| 23.5 | 23.1 |
| 24 | 12.1 |
| 24.4 | 6.5 |
| 25.2 | 17.7 |
| 25.5 | 17.4 |
| 26.4 | 13.8 |
| 26.7 | 15.2 |
| 27.4 | 6.5 |
| 28.2 | 14 |
| 28.8 | 21.3 |
| 29 | 11.8 |
| 29.5 | 18.6 |
| 29.7 | 10.4 |
| 30 | 16.2 |
| 30.5 | 10.1 |

$^1$H NMR (400 MHz, DMSO-$d_6$) δ ppm 1.04-1.18 (m, 15H) 3.28 (dd, J=6.00, 2.46 Hz, 1H) 3.30-3.39 (m, 5H) 3.64 (t, J=7.52 Hz, 2H) 3.93 (br t, J=7.52 Hz, 3H) 4.11-4.28 (m, 3H) 4.39-4.51 (m, 1H) 4.66-4.80 (m, 2H) 5.11 (br d, J=3.92 Hz, 1H) 5.75 (d, J=5.81 Hz, 1H) 5.88 (d, J=5.81 Hz, 1H) 10.10 (s, 1H). $^1$H NMR was consistent with pure tebipenem pivoxil.

Example 12. Crystalline Tebipenem Pivoxil Hydrobromide (HBR) Salt Form D

Tebipenem Pivoxil (2.5 g) was dissolved in the minimum volume of t-BuOH (25 vol, 62.5 ml) while stirring at 50° C., 600 rpm using a magnetic stirrer bar in a Polar Bear device. The sample was treated with 1 mol eq. of acid stock (1 M HBr aq. in THF, 4 ml), then frozen in a dry ice/acetone bath and lyophilised for 16 hours. The resulting white solid was crushed in a pestle and mortar, and dried in a vacuum oven at 60° C., 4 hrs. Once dried, the material (1.2 g) was placed into a 20 ml scintillation vial and stirred using a magnetic stirrer bar in diethyl ether (12.5 vol, 15 ml) at 50° C., 500 rpm, 30 minutes. The samples were subsequently cooled from 50 to 5° C. at 0.2° C./min and then stirred at 25° C. for 24 hours. The suspension obtained was filtered into a Buchner flask and dried under vacuum for 20 minutes.

TABLE 17

Solid-state characterisation of Tebipenem Pivoxil HBr Form D

| | |
|---|---|
| XRPD | Form D |
| $^1$H NMR | Consistent with HBr salt Form B No residual solvent. |
| HPLC (%, AUC) Method B | 98.8% |
| DSC | Broad endotherm from RT to 100° C. (37.4° C., onset, 5 J/g). Exotherm during degradation at 162.8° C. (onset). |
| TGA | 0.5% wt. loss from RT to 100° C. No other events until degradation. |
| XRPD analysis post storage at 40° C./75% RH or 25° C./97% for 1 wk | Converted to HBr Form B within 1 week at 25° C./97% RH, and RH deliquesced at 40° C./75% RH within 1 week. |
| Anion IC | 0.97 eq. Br |
| KF | 0.2% water |
| GVS and XRPD post-GVS | Sample shows an initial uptake of 3.0% wt from 40 to 90% RH, then reversible uptake and loss. Total of 4.0-4.5% wt uptake 0 to 90% RH. XRPD post-GVS showed a mixture of HBr Form B and Form D |
| VT-XRPD | No form changes during or post-VT-XRPD |
| VH-XRPD | No form changes during or post-VH-XRPD |

Figure 23:
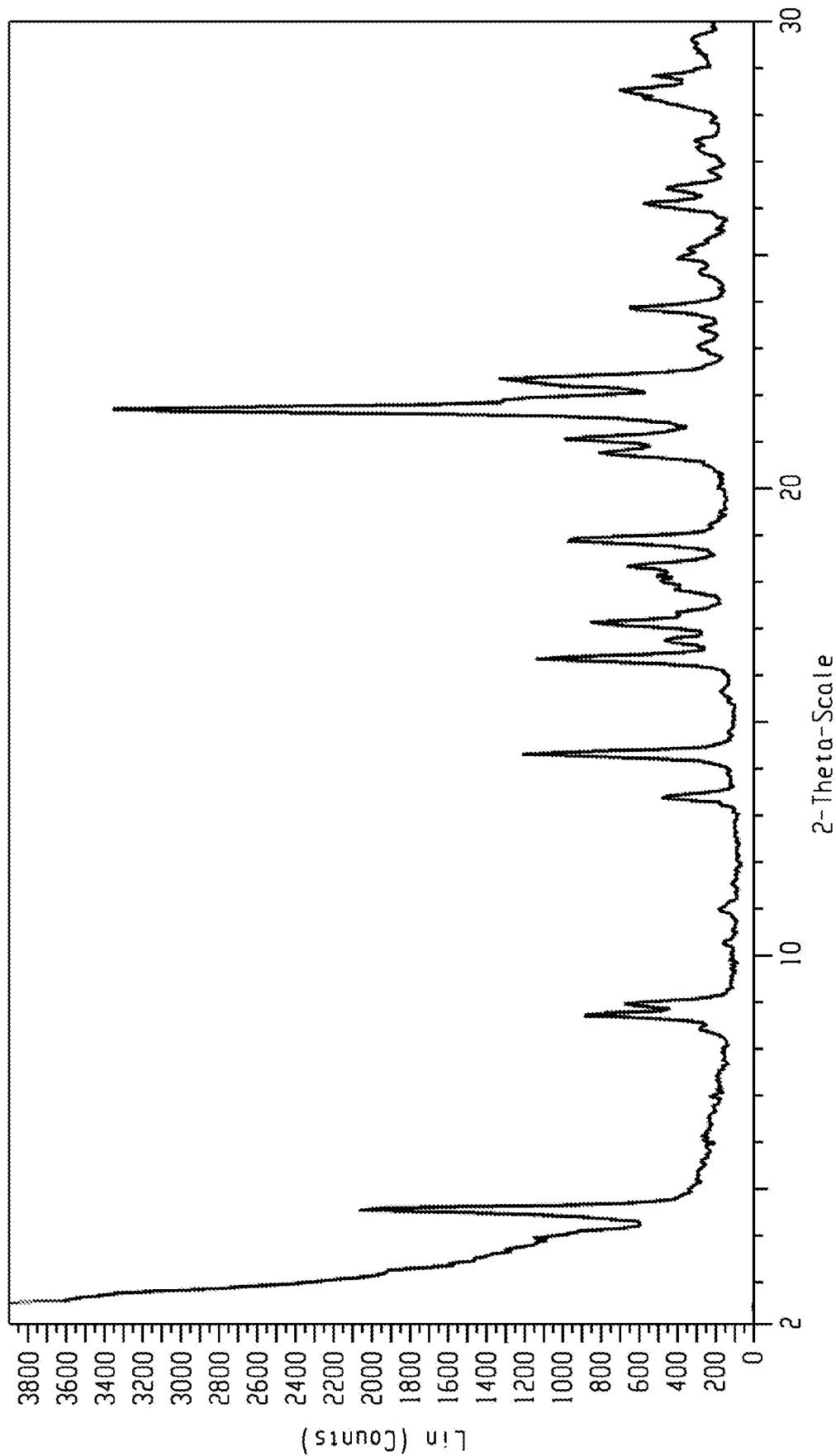
FIG. 23. XRPD diffractogram of crystalline tebipenem pivoxil hydrobromide salt Form D.
Figure 24:
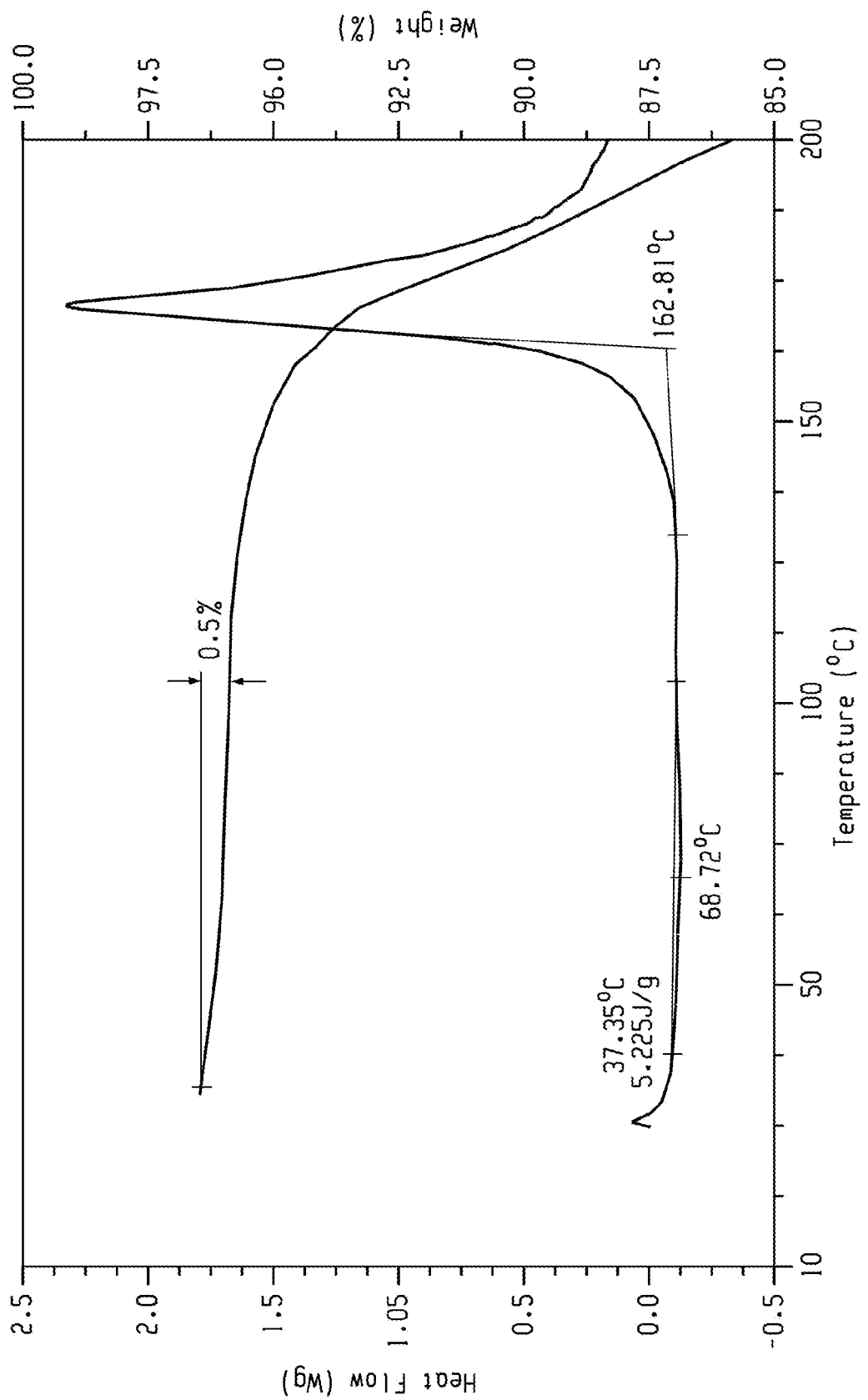
FIG. 24. DSC and TGA profiles of crystalline tebipenem pivoxil hydrobromide salt Form D.

Characteristic peaks of the XRPD diffractogram are listed in Table 18 and the XRPD diffractogram is provided at FIG. 23.

TABLE 18

Peak listing for XRPD diffractogram of HBr Form D

| Angle (2-Theta °) | Intensity (%) |
|---|---|
| 4.4 | 61.7 |
| 8.3 | 9.1 |
| 8.6 | 27 |
| 8.8 | 21.1 |
| 10.2 | 5.4 |
| 10.9 | 5.8 |
| 13.3 | 15.1 |
| 14.2 | 36.9 |
| 15.6 | 5.5 |
| 16.3 | 34 |
| 16.7 | 14.4 |
| 17.1 | 25.9 |
| 17.3 | 13.5 |
| 17.8 | 12.7 |
| 18 | 15.4 |
| 18.3 | 19 |
| 18.8 | 29.8 |
| 20.7 | 24.6 |
| 21 | 30.3 |
| 21.7 | 100 |
| 22.3 | 40.3 |
| 23 | 9.7 |
| 23.4 | 9.3 |
| 23.9 | 20.2 |
| 24.6 | 9.4 |
| 24.9 | 12.5 |
| 25.2 | 11.3 |
| 26.1 | 17.7 |
| 26.5 | 14.2 |
| 26.8 | 7.5 |
| 27.3 | 9.4 |
| 27.5 | 9.8 |
| 28.6 | 21.9 |
| 28.9 | 16.5 |
| 29.7 | 10.8 |

$^1$H NMR (400 MHz, DMSO-d$_6$) δ ppm 1.04-1.21 (m, 15H) 3.28 (dd, J=5.94, 2.27 Hz, 1H) 3.30-3.52 (m, 4H) 3.65 (t, J=7.52 Hz, 2H) 3.88-4.01 (m, 3H) 4.19 (br dd, J=9.22, 2.02 Hz, 3H) 4.45 (br d, J=5.18 Hz, 1H) 4.66-4.81 (m, 2H) 4.95-5.28 (m, 1H) 5.75 (d, J=5.81 Hz, 1H) 5.88 (d, J=5.94 Hz, 1H) 10.11 (br s, 1H). $^1$H NMR was consistent with pure tebipenem pivoxil.

Example 13. Crystalline Tebipenem Pivoxil Edisylate (EDSA) Salt Form A

Tebipenem pivoxil (30 mg) was dissolved in MeCN (320 μL). The counterion (1 M ethane disulfonic acid stock solution in THF) was added to 0.5 mol eq. and stirred at 25° C., 500 rpm using a magnetic stir bar in a Polar Bear device for 20 minutes. The sample was then cooled to 5° C. over 2 hours (0.25° C./min) and maintained at 5° C. for ~1 hour. A precipitate was obtained which was filtered using a fritted filter and air-dried on a filter block at ambient for 15 minutes. The XRPD diffractogram for tebipenem pivoxil edisylate crystalline Form A prepared by this method is shown in FIG. 16 and the peak listing is provided in Table 19. The crystalline material was found to be 94.6% pure by HPLC.

TABLE 19

Characteristic angles (2θ) of Tebipenem Pivoxil Edisylate Salt Form A

| Characteristic angle (°) | Relative intensity (%) |
|---|---|
| 4.1 | 100 |
| 5.0 | 80.7 |
| 7.7 | 20.9 |
| 8.2 | 52.8 |
| 8.5 | 23.4 |
| 9.5 | 21.2 |
| 10.1 | 27.7 |
| 13.1 | 16.8 |
| 13.5 | 15.1 |
| 15.4 | 22.9 |
| 16 | 22 |
| 16.9 | 27 |
| 17.3 | 32.1 |
| 18 | 37.4 |
| 19.1 | 32.1 |
| 20.3 | 47.6 |
| 20.7 | 46.2 |
| 21.2 | 62.9 |
| 22.7 | 16.6 |
| 23.1 | 25.1 |
| 24.5 | 23.3 |

TABLE 19-continued

Characteristic angles (2θ) of Tebipenem Pivoxil Edisylate Salt Form A

| Characteristic angle (°) | Relative intensity (%) |
|---|---|
| 25.7 | 24.6 |
| 27.3 | 31.4 |
| 28.8 | 20.3 |

The DSC profile for crystalline tebipenem pivoxil edisylate salt Form A (FIG. 17) shows a broad melting endotherm having an onset at 56.3° C. with a minima at 79.3° C. and an enthalpy of fusion of 69 J/g and a small endotherm having an onset of 144.5° C. with a minima of 157.5° C. and an enthalpy of fusion of 14 J/g.

The TGA for tebipenem pivoxil edisylate salt form A (also shown in FIG. 17) shows a 4.0% weight loss from room temperature to 160° C. No other thermal events were noted prior to the onset of degradation.

$^1$H NMR (400 MHz, DMSO-$d_6$) δ ppm 1.05-1.19 (m, 15H) 2.01-2.08 (m, 1H) 2.07 (s, 1H) 2.61 (s, 2H) 3.27 (dd, J=6.19, 2.78 Hz, 1H) 3.34 (s, 17H) 3.62 (t, J=7.52 Hz, 2H) 3.89-4.01 (m, 3H) 4.09-4.24 (m, 3H) 4.39-4.49 (m, 1H) 4.70 (td, J=8.87, 4.36 Hz, 2H) 5.11 (d, J=5.18 Hz, 1H) 5.75 (d, J=5.94 Hz, 1H) 5.88 (d, J=5.94 Hz, 1H) 10.12 (br s, 1H). $^1$H NMR was consistent with pure tebipenem pivoxil. Approximately 0.47 equivalents of the edisylate counterion and 0.24 equivalents MeCN solvent were observed. Three days post storage at 40° C. and 75% relative humidity the sample was found to be deliquesced.

Example 14. Large Scale Preparation of Tebipenem Pivoxil HBR

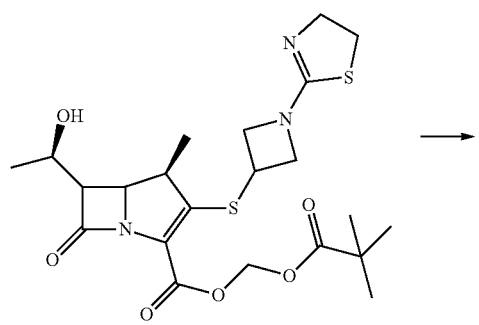

→

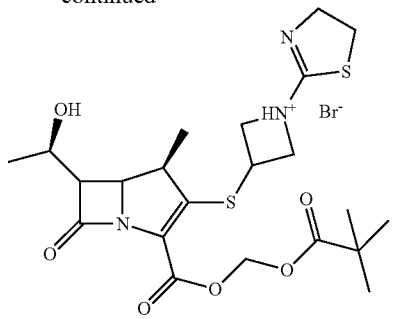

In a 20 L reactor flask, equipped with thermometer and dropping funnel and mechanical stirring, immersed in an empty tub, tebipenem pivoxil (1.00 kg, 2.01 mol, 1.0 eq, 99.5% HPLC purity) was dissolved in 8.0 L acetonitrile. The solution (fully transparent) was stirred at rt. In a separate round bottom flask, the HBr in acetonitrile solution was prepared. 1.5 L acetonitrile was stirred in a RBF, then cooled in an icebath. At 5° C. was added 230 mL HBr solution (48% aq.) (1.0 eq HBr with respect to tebipenem pivoxil) at such a rate that temp. did not exceed 10° C. (~15 mins) The HBr solution (T adjusted to 0° C. prior to addition) was added at a rate of 33 mL min-1 (requiring 1 h total) to the solution of tebipenem pivoxil, from a 1 L dropping funnel (the funnel was replenished during addition). After approximately 0.5 L of the HBr solution was added, precipitation was evident. The mixture was cooled to 5° C. and stirred 1 h. The mixture was filtered over a large P3 glass filter and the cake was washed with 1 L acetonitrile at RT. The filter cake was dried on the filter 30 min, then transferred to dish and dried under vacuum with N2 bleed. The tebipenem pivoxil hydrobromide (0.970 g, 1.68 mol, 83.6% yield, 99.2% HPLC purity) was determined to be dry by NMR (not shown) and packaged in a large 2 L jar and stored 2-8 5° C.

Example 15. Stability Studies

Salt screen results using Tebipenem Pivoxil free base are summarized in Table 20.

TABLE 20

| | Salt screen results using free base | | |
|---|---|---|---|
| | Salt | | |
| | Malate | Maleate | Esylate |
| | Example No. | | |
| | Example 5 | Example 4 | Example 1 |
| HPLC (AUC) | 97.3% (Method A) | 99.3% (Method A) | 99.0% (Method A) |
| | 99.3% (Method B) | 99.8% (Method B) | 99.8% (Method B) |
| XRPD and HPLC analysis post-storage at 40° C./75% RH 1 week | Deliquesced, orange liquid | MAE Form B 78.6% (Method A) | ESA Form A(yellow solid) 80.7% (Method A) |

Characterisation of Tebipenem Pivoxil edisylate salt obtained from screens on free form in acetonitrile is summarized in Table 21.

TABLE 1

Characterization of Tebipenem Pivoxil edisylate salt obtained from screens on free form in acetonitrile

| | |
|---|---|
| HPLC (%, AUC), Method A | 94.6% |
| XRPD analysis post storage at 40° C./75% RH 1 week | Deliquesced (within 3 days) |

TABLE 2

Results from repeated salt screens using the free base in acetonitrile

| | Example No. | | |
|---|---|---|---|
| | Example 4 | Example 2 | Example 1 |
| XRPD | Maleate Form B | Ketoglutarate Form A | Esylate Form A |
| XRPD and HPLC analysis post-storage at 40° C./75% RH for 1 week | Maleate Form B 90.2% (Method A) | Deliquesced | Deliquesced/gum |

While the subject matter of this disclosure has been described with reference to exemplified embodiments, it will be understood by those skilled in the art that various changes may be made and equivalents may be substituted for elements thereof without departing from the scope of the disclosure. In addition, many modifications may be made to adapt a particular situation or material to the teachings without departing from the essential scope thereof. Therefore, it is intended that the disclosure not be limited to the particular disclosed embodiments, but will include all embodiments falling within the scope of the appended claims.

What is claimed is:

1. A crystalline tebipenem pivoxil hydrobromide salt form, wherein the XRPD of the form, obtained from a Cu Kα source, has the characteristic 2θ values of FIG. 21.

2. A crystalline tebipenem pivoxil hydrobromide salt form characterized by an XRPD diffractogram obtained from a Cu Kα source which comprises peaks at 2θ values of 12.0, 13.1, 16.3, 21.7, and 23.5+/−0.2 degrees 2θ; or 8.7, 9.3, 17.3, 20.8, and 22.6+/−0.2 degrees 2θ.

3. A crystalline tebipenem pivoxil hydrobromide salt form of claim 2 characterized by an XRPD diffractogram obtained from a Cu Kα source which comprises peaks at 2θ values of 8.7, 9.3, 12.0, 13.1, 16.3, 17.3, 20.8, 21.7, 22.6, and 23.5.

Figure 22:
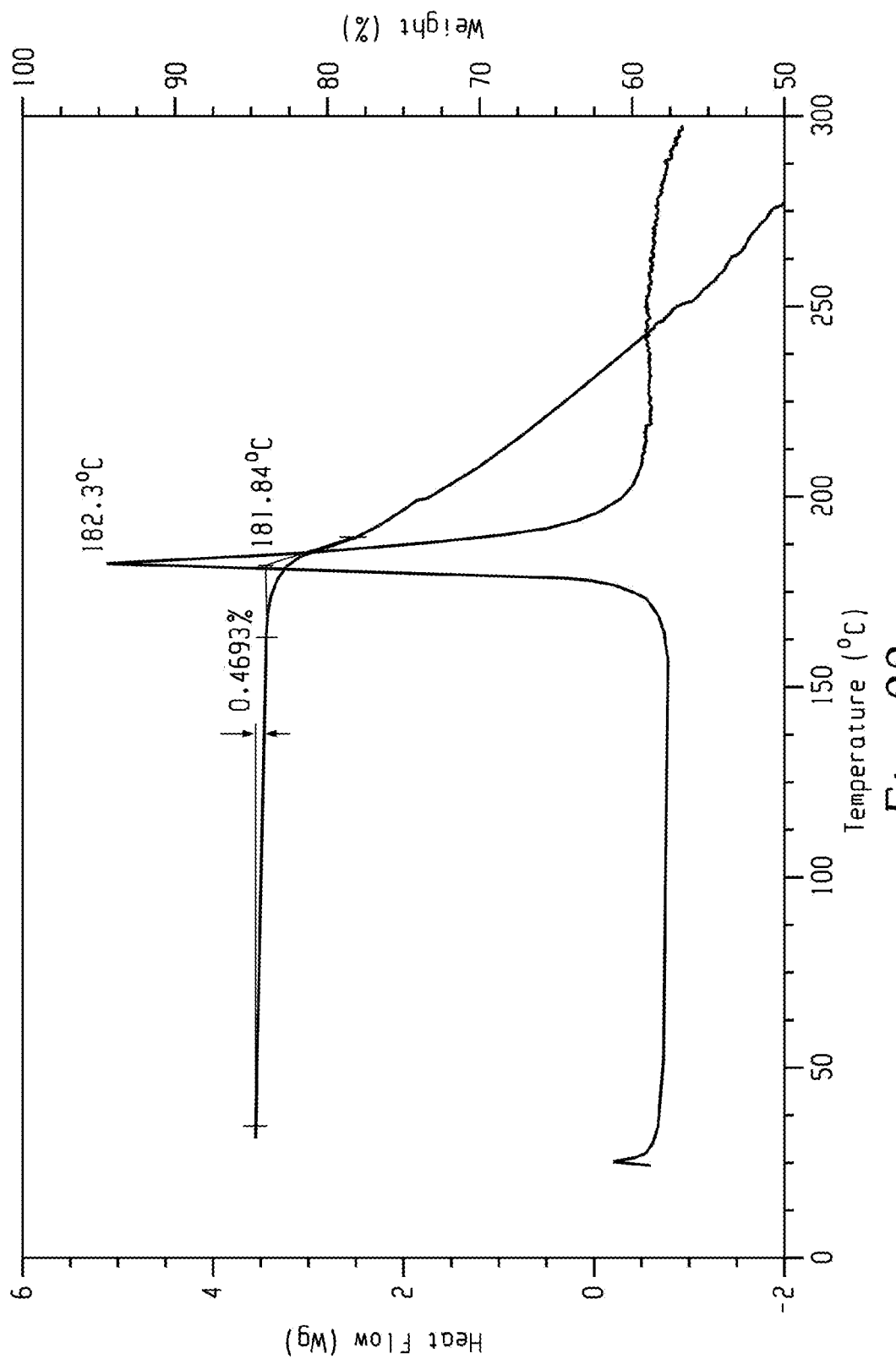
FIG. 22. DSC and TGA profiles of crystalline tebipenem pivoxil hydrobromide salt Form C.

4. The crystalline tebipenem pivoxil hydrobromide salt form of claim 2, additionally characterized by a DSC profile substantially as shown in FIG. 22.

5. The crystalline tebipenem pivoxil hydrobromide salt form of claim 2 additionally characterized by a DSC profile having an exotherm with an onset at 179.5° C. and a maxima at 182.3° C.

6. A pharmaceutical composition comprising a tebipenem pivoxil salt and a physiologically acceptable carrier, wherein the tebipenem pivoxil salt comprises at least 90% of the crystalline tebipenem pivoxil hydrobromide salt form of claim 2.

7. A dosage form comprising the pharmaceutical composition of claim 6, wherein the dosage form is an intravenous, injectable, topical, or oral dosage form.

8. The dosage form of claim 7, wherein the dosage form is in an oral dosage form in the form of a tablet or capsule.

9. A method for treating a patient infected with a bacterial infection, comprising administering to the patient a therapeutically effective amount of the crystalline tebipenem pivoxil hydrobromide salt form of claim 2.

10. The method according to claim 9, wherein the patient is a human.

11. The method of claim 10, wherein the bacterial infection is a urinary tract infection.

12. The pharmaceutical composition of claim 6, wherein the pharmaceutical composition contains a second active agent in addition to the crystalline tebipenem pivoxil hydrobromide salt form.

13. The pharmaceutical composition of claim 12, wherein the second active agent is an antibiotic.

14. The method of claim 9, wherein a second active agent is administered to the patient in combination with the crystalline tebipenem pivoxil hydrobromide salt form.

15. The method of claim 14, wherein the second active agent is an antibiotic.

16. The method of claim 9, wherein the bacterial infection is a Gram negative bacterial infection, an *E. coli* infection, a *Klebsiella pneumoniae* infection, an *Acinetobacter baumannii* infection, a *Pseudomonas aeruginosa* infection, a *Neisseria gonorrhoeae* infection, or a *Yersinia pestis* infection.

* * * * *